United States Patent [19]

Blaser et al.

[11] Patent Number: 5,874,300
[45] Date of Patent: Feb. 23, 1999

[54] CAMPYLOBACTER JEJUNI ANTIGENS AND METHODS FOR THEIR PRODUCTION AND USE

[75] Inventors: Martin J. Blaser; Zhiheng Pei, both of Nashville, Tenn.

[73] Assignee: Enteric Research Laboratories

[21] Appl. No.: 402,804

[22] Filed: Mar. 13, 1995

Related U.S. Application Data

[63] Continuation of Ser. No. 114,420, Aug. 30, 1993, abandoned, which is a continuation-in-part of Ser. No. 112,387, Aug. 27, 1993, abandoned.

[51] Int. Cl.$^6$ .......................... C12N 15/31; C12N 15/63; C12N 15/70; C12N 15/79
[52] U.S. Cl. .......................... 435/325; 435/348; 435/362; 435/365; 435/367; 435/252.3; 435/252.33; 435/252.31; 435/254.2; 435/254.21; 435/320.1; 435/69.3; 536/23.7
[58] Field of Search .......................... 435/69.3, 252.3, 435/320.1, 348, 362, 365, 325, 367, 250.33, 252.31, 254.2, 254.21, 62.3; 536/23.7

[56] References Cited

U.S. PATENT DOCUMENTS

| | | |
|---|---|---|
| 4,404,194 | 9/1983 | Arala-Chaves . |
| 4,683,195 | 7/1987 | Mullis et al. . |
| 4,704,362 | 11/1987 | Itakura et al. . |
| 4,785,086 | 11/1988 | Rashtchian et al. . |
| 4,800,159 | 1/1989 | Mullis et al. . |
| 4,879,213 | 11/1989 | Fox et al. . |
| 4,882,271 | 11/1989 | Evans et al. . |
| 4,965,188 | 10/1990 | Mullis et al. . |
| 5,200,344 | 4/1993 | Blaser et al. . |
| 5,459,041 | 10/1995 | Blaser . |

FOREIGN PATENT DOCUMENTS

| | | |
|---|---|---|
| 90/14837 | 12/1990 | WIPO . |
| 92/08485 | 5/1992 | WIPO . |

OTHER PUBLICATIONS

Blaser, et al., *N. Eng. J. Med.* (1981) 305:1444–1452.
Blaser, et al., *Ann. Intern. Med.* (1983) 98:360–365.
Glass, et al., *J. Infect. Dis.* (1983) 148:292–296.
Blaser, et al., *Epidemiologic Reviews* (1983) 5:157–176.
Blaser, et al., *Infect. Immun.* (1984) 44:292–298.
Black, et al., *J. Infect. Dis.* (1988) 157:472–479.
Perlman, et al., "Humoral Immune Response to Campylobacter Jejuni in Human Volunteers" Abst./87th Ann. Meet. Amer. Soc. for Microbio. (Mar. 1987).
Perlman, et al., "Immunity to Campylobacter Jejuni Following Oral Challenge to Volunteers" Abst./4th Int'l Wkshp on Campylobacter Infec. (Jun. 1987).
Blaser, et al., *JAMA* (1987) 257:43–46.
Pei, et al., *J. Biol. Chem.* (1988) 263:6416–6420.
Miotti, *Eur. J. Epidemiol.* (1987) 3:356–364.
Blaser, et al., *Infection and Immunity* (1984) vol. 43, No. 3, pp. 986–993.
Dunn, et al., *Infection and Immunity*, vol. 55, No. 7, pp. 1564–1572 (Jul. 1987).
Ames GFL, *J. Biol. Chem.* (1974) 249:634–644.
Oakley, et al., *Anal. Biochem.* (1980) 105:361–363.
Pei, et al., *J. Clin. Invest.* (1990) 85:1036–1043.
Markwell, et al., *Anal. Biochem.* (1978) 87:206–210.
Willoughby, et al., *Anal. Biochem.* (1983) 130:353–358.
Towbin, et al., *Proc. Nat'l. Acad. Sci.* (1979) 76:4350–54.
Jones BN, *J. Liq. Chromatogr.* (1981) 4:565–568.
Burnette, et al., *Biochem.* (1981) 112:195–203.
Black, et al., *Dev. Biol. Stand* (1983) 53:9–14 (Abstract Only).
Eldridge, et al., *Curr. Top. Microbiol. Immunol.* (1989) 146:59.
Klugman, et al., *The Lancet*, Nov. 21, 1987, pp. 1165–1169.
Dubreuil, et al.,*J. Clin. Microbiol.* (1990) 28(6):1321–1328.
Arnon, *Synthetic Vaccines* I:L 83–92, CRC Press, Inc.
Birnboim and Doly, *Nucleic Acids. Res.*, 7:1513–1523 (1979).
Carbonell, et al., *J. Virol.*, 56:153 (1985).
Feinberg and Bogelstein, *Anal. Biochem.*, 132:6–13 (1983).
Fraser, et al., *In vitro Cell. Dev. Biol.*, 25:225 (1989).
Kunkel, et al., *Methods Enzymol.*, 154:367 (1987).
Labigne–Roussel, et al., *J. Bacteriol.*, 170:1704 (1988).
Harlow & Lane, *Antibodies: A Laboratory Manual*, Cold Spring Harbor Lab. (1988) (Table of Contents only).
Sambrook, et al., *Molecular Cloning: A Lab Manual* (1989) (Table of Contents only).
Sanger, et al., *Proc. Natl. Acad. Sci. U.S.A.*, 71:1342–1346.32 (1977).
Smith, et al., *Mol. Cell. Biol.*, 3:2156 (1983).
Summers & Smith, *Texas Agri. Exp. Bull. No. 1555* (1987) (Table of Contents only).
Wright, *Nature*, 321:718 (1986).
Pei, et al., *J. Biol. Chem.*, 266:16363–16369 (1991).
Ferrero, et al., *J. Bacteriol.*, 174:4212 (1992).
Kervella, et al., *Infection and Immunity*, vol. 61 8:3440–3448 (1993).
P.J. Ramaniuk et al. FEMS Microbiology Letters 43:331–335 1987.
J.L. Fauchere et al. Res. Microbiol. 140:379–392 Oct. 1989.
C.C. Lee et al. Science 238:1288–1291 Mar. 1988.
J.U. Bowie et al. Science 247:1306–1310 Mar. 1990.
V. Kumar et al. PNAS 87:1337–1341 Feb. 1990.
R.A. Young PNAS 80:1194–1198 Mar. 1983.
G.D. Pennock et al. Mol. Cell. Biology 4(3):399–406 Mar. 1984.

(List continued on next page.)

*Primary Examiner*—Anthony C. Caputa
*Attorney, Agent, or Firm*—Ostrolenk, Faber, Gerb & Soffen, LLP

[57] ABSTRACT

The present invention provides an isolated nucleic acid encoding an approximately 26 kilodalton antigen, PEB1A, of *Campylobacter jejuni*, or an antigenic fragment thereof, wherein the antigen is associated with diarrheal disease. The present invention also provides methods of detecting the presence of a *Campylobacter jejuni* strain possessing the PEB1A antigen in a subject. Vaccines and treatments for *C. jejuni* infection are provided, as is a mutant *C. jejuni* not expressing a functional PEB1A antigen.

18 Claims, 8 Drawing Sheets

OTHER PUBLICATIONS

Blaser, et al., *Infection and Immunity* (1983) 42(1) pp. 276–284.

Blaser, et al., *Infection and Immunity* (1986) 53(1) pp. 47–52.

Meinersmann, et al., *Current Microbiology* (1990) 21(1) pp. 17–21.

De Melo, et al., *Infection and Immunity* (1990) 58(6) pp. 1749–1756.

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 82 base pairs
        ( B ) TYPE: nucleic acid
        ( C ) STRANDEDNESS: double
        ( D ) TOPOLOGY: circular ( i x ) FEATURE:
        ( A ) NAME/KEY: CDS
        ( B ) LOCATION: 2..64

( x i ) SEQUENCE DESCRIPTION: SEQ ID NO:1:

```
G  CAT  TTA  AAA  CCT  ATG  AGC  TTA  AAA  GAA  ATT  AAA  AAA  GAA  ATT  GTA          46
   His  Leu  Lys  Pro  Met  Ser  Leu  Lys  Glu  Ile  Lys  Lys  Glu  Ile  Val
   1                  5                        10                       15

AAT  TTT  ATT  GAT  CAG  GAT  TAATAAAGG  AAAATTGC                                       82
Asn  Phe  Ile  Asp  Gln  Asp
                    20
```

( 2 ) INFORMATION FOR SEQ ID NO:2:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
His  Leu  Lys  Pro  Met  Ser  Leu  Lys  Glu  Ile  Lys  Lys  Glu  Ile  Val  Asn
1                  5                        10                       15

Phe  Ile  Asp  Gln  Asp
                    20
```

( 2 ) INFORMATION FOR SEQ ID NO:3:

( i ) SEQUENCE CHARACTERISTICS:
        ( A ) LENGTH: 941 base pairs
        ( B ) TYPE: nucleic acid
        ( C ) STRANDEDNESS: double
        ( D ) TOPOLOGY: circular ( i x ) FEATURE:
        ( A ) NAME/KEY: CDS
        ( B ) LOCATION: 19..810

( x i ) SEQUENCE DESCRIPTION: SEQ ID NO:3:

```
TAATAAAGG AAAATTGC ATG GAA AAA AAA ATA ACT CCT AGC GAA TTG GAA            51
                     Met Glu Lys Lys Ile Thr Pro Ser Glu Leu Glu
                      1           5                          10

CTT AAT GAA TTT ATA AAA ATT ATC AAC GAA ATG AGT GGT ATT GAT TTA           99
Leu Asn Glu Phe Ile Lys Ile Ile Asn Glu Met Ser Gly Ile Asp Leu
             15                  20                      25

ACC GAT AAA AAA AAT ATA CTA GCT TTA AAG TTG AAT AAA TTT CTT GAA          147
Thr Asp Lys Lys Asn Ile Leu Ala Leu Lys Leu Asn Lys Phe Leu Glu
         30                  35                  40

GGA ACT AAT ACT AAA AAT TTT TCC GAA TTT TTG GGA AAA TTA AAA AGC          195
Gly Thr Asn Thr Lys Asn Phe Ser Glu Phe Leu Gly Lys Leu Lys Ser
 45                  50                  55

AAT AGA CAA CTT AAA CAA GAA ACT TTA GAT TTT GTA ACC ATA GGT GAA          243
Asn Arg Gln Leu Lys Gln Glu Thr Leu Asp Phe Val Thr Ile Gly Glu
 60              65                  70                      75

ACT TAT TTT TTA AGA GAA TTG GCT CAA TTG AAA GAA ATA ATT TAT TAT          291
Thr Tyr Phe Leu Arg Glu Leu Ala Gln Leu Lys Glu Ile Ile Tyr Tyr
             80                  85                      90

GCC AAA AGC TTA GAA AAG AGA GTA AAT ATC CTA AGC GCC CCT TGT TCA          339
Ala Lys Ser Leu Glu Lys Arg Val Asn Ile Leu Ser Ala Pro Cys Ser
             95                 100                 105

AGT GGA GAA GAA GTA TAT TCT TTG GCA TTA TTG GCT GCA CAG AAT TTT          387
Ser Gly Glu Glu Val Tyr Ser Leu Ala Leu Leu Ala Ala Gln Asn Phe
        110                 115                 120

ATT AAA GAT ATG TAT ATT TTA GGC GTT GAT ATT AAT TCA AGT GTG ATT          435
Ile Lys Asp Met Tyr Ile Leu Gly Val Asp Ile Asn Ser Ser Val Ile
        125                 130                 135

GAA AAA GCA AAA CTT GGA AAA TAT CAA GGA AGA ACT TTA CAG CGA TTG          483
Glu Lys Ala Lys Leu Gly Lys Tyr Gln Gly Arg Thr Leu Gln Arg Leu
140                 145                 150                 155

AGC GAG AGT GAA AAA AGA AGG TTT TTT TTA GAA AGC GAA GAT AAA TTT          531
Ser Glu Ser Glu Lys Arg Arg Phe Phe Leu Glu Ser Glu Asp Lys Phe
                160                 165                 170

TAT ACT ATT AAT AAA AAT GAG CTT TGT ACT TGT AAA TTT GAA CTT TGC          579
Tyr Thr Ile Asn Lys Asn Glu Leu Cys Thr Cys Lys Phe Glu Leu Cys
            175                 180                 185

AAT GTT TTT GAA GAA AAA TTT TCA AGA TTG GGA AAA TTT GAT ATT ATA          627
Asn Val Phe Glu Glu Lys Phe Ser Arg Leu Gly Lys Phe Asp Ile Ile
        190                 195                 200

GCT TCT AGA AAT ATG ATT ATT TAT TTT GAT CAT GAA TCA AAA CTA AAA          675
Ala Ser Arg Asn Met Ile Ile Tyr Phe Asp His Glu Ser Lys Leu Lys
        205                 210                 215

CTT ATG GAG AGG TTT CAT AGA ATT TTA AAT GAT AAA GGA AGG CTT TAT          723
Leu Met Glu Arg Phe His Arg Ile Leu Asn Asp Lys Gly Arg Leu Tyr
220                 225                 230                 235

GTT GGC AAT GCT GAT TTA ATT CCA GAG ACT ATT TAT TTT AAA AAG ATT          771
Val Gly Asn Ala Asp Leu Ile Pro Glu Thr Ile Tyr Phe Lys Lys Ile
                240                 245                 250

TCT CTC CAA GAG GTG TTT ACT ATG AAA AAG TAT AAA TTC TAAAAATTAC           820
Ser Leu Gln Glu Val Phe Thr Met Lys Lys Tyr Lys Phe
```

|       | 255 |       |       | 260 |       |       |       |       |       |
|-------|-----|-------|-------|-----|-------|-------|-------|-------|-------|
| TAAAAGTTAC | ACTTTGGAAA | TTTATTAGTA | AAAATAAGTT | ACATTTTGAA | GTAGTTTTCT | 880 |
| TTATTTAATG | ATAAAATAAT | TTCAATTAAT | TTTATATTTA | GCTAAAAATA | AAGGAAAAAA | 940 |
| C | | | | | | 941 |

( 2 ) INFORMATION FOR SEQ ID NO:4:

( i ) SEQUENCE CHARACTERISTICS:
  ( A ) LENGTH: 264 amino acids
  ( B ) TYPE: amino acid
  ( D ) TOPOLOGY: linear ( i i ) MOLECULE TYPE: protein ( x i ) SEQUENCE DESCRIPTION: SEQ ID NO:4:

```
Met Glu Lys Lys Ile Thr Pro Ser Glu Leu Glu Leu Asn Glu Phe Ile
 1               5                  10                  15
Lys Ile Ile Asn Glu Met Ser Gly Ile Asp Leu Thr Asp Lys Lys Asn
             20                  25                  30
Ile Leu Ala Leu Lys Leu Asn Lys Phe Leu Glu Gly Thr Asn Thr Lys
         35                  40                  45
Asn Phe Ser Glu Phe Leu Gly Lys Leu Lys Ser Asn Arg Gln Leu Lys
     50                  55                  60
Gln Glu Thr Leu Asp Phe Val Thr Ile Gly Glu Thr Tyr Phe Leu Arg
 65                  70                  75                  80
Glu Leu Ala Gln Leu Lys Glu Ile Ile Tyr Tyr Ala Lys Ser Leu Glu
                 85                  90                  95
Lys Arg Val Asn Ile Leu Ser Ala Pro Cys Ser Ser Gly Glu Glu Val
            100                 105                 110
Tyr Ser Leu Ala Leu Leu Ala Ala Gln Asn Phe Ile Lys Asp Met Tyr
        115                 120                 125
Ile Leu Gly Val Asp Ile Asn Ser Ser Val Ile Glu Lys Ala Lys Leu
    130                 135                 140
Gly Lys Tyr Gln Gly Arg Thr Leu Gln Arg Leu Ser Glu Ser Glu Lys
145                 150                 155                 160
Arg Arg Phe Phe Leu Glu Ser Glu Asp Lys Phe Tyr Thr Ile Asn Lys
                165                 170                 175
Asn Glu Leu Cys Thr Cys Lys Phe Glu Leu Cys Asn Val Phe Glu Glu
            180                 185                 190
Lys Phe Ser Arg Leu Gly Lys Phe Asp Ile Ile Ala Ser Arg Asn Met
        195                 200                 205
Ile Ile Tyr Phe Asp His Glu Ser Lys Leu Lys Leu Met Glu Arg Phe
    210                 215                 220
His Arg Ile Leu Asn Asp Lys Gly Arg Leu Tyr Val Gly Asn Ala Asp
225                 230                 235                 240
Leu Ile Pro Glu Thr Ile Tyr Phe Lys Lys Ile Ser Leu Gln Glu Val
                245                 250                 255
Phe Thr Met Lys Lys Tyr Lys Phe
                260
```

( 2 ) INFORMATION FOR SEQ ID NO:5:

( i ) SEQUENCE CHARACTERISTICS:
  ( A ) LENGTH: 881 base pairs
  ( B ) TYPE: nucleic acid
  ( C ) STRANDEDNESS: double
  ( D ) TOPOLOGY: circular (ix) FEATURE:
    (A) NAME/KEY: CDS
    (B) LOCATION: 132..857

(xi) SEQUENCE DESCRIPTION: SEQ ID NO:5:

```
TAAAAATTAC TAAAAGTTAC ACTTTGGAAA TTTATTAGTA AAAATAAGTT ACATTTGAA      60

GTAGTTTTCT TTATTTAATG ATAAAATAAT TTCAATTAAT TTTATATTTA GCTAAAAATA    120

AAGGAAAAAA C TTG ATT GAA TTA AAA AAT GTA AAC AAA TAC TAC GGA ACT    170
            Leu Ile Glu Leu Lys Asn Val Asn Lys Tyr Tyr Gly Thr
              1               5                      10

CAT CAT GTT CTA AAG ATA TTT AAT CTT TCT GTT AAA GAA GGT GAG AAG     218
His His Val Leu Lys Ile Phe Asn Leu Ser Val Lys Glu Gly Glu Lys
         15              20              25

CTT GTT ATT ATA GGT CCA AGT GGA AGT GGA AAA AGT ACA ACT ATC CGT     266
Leu Val Ile Ile Gly Pro Ser Gly Ser Gly Lys Ser Thr Thr Ile Arg
 30              35              40                      45

TGC ATG AAT GGG CTT GAA GAA GTT AGT TCA GGA GAG GTC GTA GTT AAC     314
Cys Met Asn Gly Leu Glu Glu Val Ser Ser Gly Glu Val Val Val Asn
             50              55                      60

AAT CTT GTT TTA AAT CAT AAA AAT AAA ATT GAA ATT TGC CGA AAA TAT     362
Asn Leu Val Leu Asn His Lys Asn Lys Ile Glu Ile Cys Arg Lys Tyr
                 65              70              75

TGT GCA ATG GTT TTT CAG CAT TTT AAT TTA TAT CCA CAT ATG ACG GTT    410
Cys Ala Met Val Phe Gln His Phe Asn Leu Tyr Pro His Met Thr Val
             80              85              90

TTG CAA AAT TTG ACC TTA GCT CCA ATG AAA CTT CAA AAA AAA TCT AAA     458
Leu Gln Asn Leu Thr Leu Ala Pro Met Lys Leu Gln Lys Lys Ser Lys
         95             100             105

AAA GAA GCT GAA GAA ACA GCT TTT AAG TAT TTA AAA GTT GTA GGT TTG     506
Lys Glu Ala Glu Glu Thr Ala Phe Lys Tyr Leu Lys Val Val Gly Leu
110             115             120             125

CTG GAT AAA GCA AAT GTT TAT CCA GCA ACC CTT TCA GGT GGA CAA CAA     554
Leu Asp Lys Ala Asn Val Tyr Pro Ala Thr Leu Ser Gly Gly Gln Gln
                130             135             140

CAA CGC GTT GCT ATA GCA AGA TCA CTT TGT ACT AAA AAA CCC TAT ATT     602
Gln Arg Val Ala Ile Ala Arg Ser Leu Cys Thr Lys Lys Pro Tyr Ile
             145             150             155

TTA TTT GAT GAA CCT ACT TCA GCC CTT GAT CCA GAA ACC ATA CAA GAG     650
Leu Phe Asp Glu Pro Thr Ser Ala Leu Asp Pro Glu Thr Ile Gln Glu
         160             165             170

GTT TTA GAT GTA ATG AAA GAA ATT TCA CAT CAA AGC AAT ACT ACC ATG     698
Val Leu Asp Val Met Lys Glu Ile Ser His Gln Ser Asn Thr Thr Met
175             180             185

GTG GTT GTT ACA CAC GAA ATG GGT TTT GCA AAA GAA GTA GCA GAT AGG     746
Val Val Val Thr His Glu Met Gly Phe Ala Lys Glu Val Ala Asp Arg
190             195             200             205

ATT ATT TTT ATG GAA GAT GGT GCT ATT GTG GAA GAA AAT ATT CCT AGT     794
Ile Ile Phe Met Glu Asp Gly Ala Ile Val Glu Glu Asn Ile Pro Ser
                210             215             220

GAA TTT TTC TCA AAT CCA AAA ACT GAA AGA GCG CGA CTC TTT TTA GGG     842
Glu Phe Phe Ser Asn Pro Lys Thr Glu Arg Ala Arg Leu Phe Leu Gly
             225             230             235

AAA ATT CTT AAA AAT TAACCAAAAT TGAAGGAGA AAAA                        881
Lys Ile Leu Lys Asn
              240
```

(2) INFORMATION FOR SEQ ID NO:6:

(i) SEQUENCE CHARACTERISTICS:
      (A) LENGTH: 242 amino acids
      (B) TYPE: amino acid (D) TOPOLOGY: linear (ii) MOLECULE TYPE: protein (xi) SEQUENCE DESCRIPTION: SEQ ID NO:6:

| Leu | Ile | Glu | Leu | Lys | Asn | Val | Asn | Lys | Tyr | Tyr | Gly | Thr | His | His | Val |
|---|---|---|---|---|---|---|---|---|---|---|---|---|---|---|---|
| 1 | | | | 5 | | | | | 10 | | | | | 15 | |
| Leu | Lys | Ile | Phe | Asn | Leu | Ser | Val | Lys | Glu | Gly | Glu | Lys | Leu | Val | Ile |
| | | | 20 | | | | | 25 | | | | | 30 | | |
| Ile | Gly | Pro | Ser | Gly | Ser | Gly | Lys | Ser | Thr | Thr | Ile | Arg | Cys | Met | Asn |
| | | | 35 | | | | | 40 | | | | | 45 | | |
| Gly | Leu | Glu | Glu | Val | Ser | Ser | Gly | Glu | Val | Val | Val | Asn | Asn | Leu | Val |
| | | | 50 | | | | | 55 | | | | | 60 | | |
| Leu | Asn | His | Lys | Asn | Lys | Ile | Glu | Ile | Cys | Arg | Lys | Tyr | Cys | Ala | Met |
| 65 | | | | | 70 | | | | | 75 | | | | | 80 |
| Val | Phe | Gln | His | Phe | Asn | Leu | Tyr | Pro | His | Met | Thr | Val | Leu | Gln | Asn |
| | | | | 85 | | | | | 90 | | | | | 95 | |
| Leu | Thr | Leu | Ala | Pro | Met | Lys | Leu | Gln | Lys | Lys | Ser | Lys | Lys | Glu | Ala |
| | | | | 100 | | | | | 105 | | | | | 110 | |
| Glu | Glu | Thr | Ala | Phe | Lys | Tyr | Leu | Lys | Val | Val | Gly | Leu | Leu | Asp | Lys |
| | | | 115 | | | | | 120 | | | | | 125 | | |
| Ala | Asn | Val | Tyr | Pro | Ala | Thr | Leu | Ser | Gly | Gly | Gln | Gln | Gln | Arg | Val |
| | | | 130 | | | | | 135 | | | | | 140 | | |
| Ala | Ile | Ala | Arg | Ser | Leu | Cys | Thr | Lys | Lys | Pro | Tyr | Ile | Leu | Phe | Asp |
| 145 | | | | | 150 | | | | | 155 | | | | | 160 |
| Glu | Pro | Thr | Ser | Ala | Leu | Asp | Pro | Glu | Thr | Ile | Gln | Glu | Val | Leu | Asp |
| | | | | 165 | | | | | 170 | | | | | 175 | |
| Val | Met | Lys | Glu | Ile | Ser | His | Gln | Ser | Asn | Thr | Thr | Met | Val | Val | Val |
| | | | | 180 | | | | | 185 | | | | | 190 | |
| Thr | His | Glu | Met | Gly | Phe | Ala | Lys | Glu | Val | Ala | Asp | Arg | Ile | Ile | Phe |
| | | | 195 | | | | | 200 | | | | | 205 | | |
| Met | Glu | Asp | Gly | Ala | Ile | Val | Glu | Glu | Asn | Ile | Pro | Ser | Glu | Phe | Phe |
| | | | 210 | | | | | 215 | | | | | 220 | | |
| Ser | Asn | Pro | Lys | Thr | Glu | Arg | Ala | Arg | Leu | Phe | Leu | Gly | Lys | Ile | Leu |
| 225 | | | | | 230 | | | | | 235 | | | | | 240 |
| Lys | Asn | | | | | | | | | | | | | | |

(2) INFORMATION FOR SEQ ID NO:7:

(i) SEQUENCE CHARACTERISTICS:
    (A) LENGTH: 805 base pairs
    (B) TYPE: nucleic acid
    (C) STRANDEDNESS: double
    (D) TOPOLOGY: circular (ix) FEATURE:
    (A) NAME/KEY: CDS
    (B) LOCATION: 25..801

(xi) SEQUENCE DESCRIPTION: SEQ ID NO:7:

```
TAACCAAAAT TGAAAGGAGA AAAA ATG GTT TTT AGA AAA TCT TTG TTA AAG              51
                           Met Val Phe Arg Lys Ser Leu Leu Lys
                             1               5

TTG GCA GTT TTT GCT CTA GGT GCT TGT GTT GCA TTT AGC AAT GCT AAT             99
Leu Ala Val Phe Ala Leu Gly Ala Cys Val Ala Phe Ser Asn Ala Asn
 10              15                  20                  25

GCA GCA GAA GGT AAA CTT GAG TCT ATT AAA TCT AAA GGA CAA TTA ATA            147
Ala Ala Glu Gly Lys Leu Glu Ser Ile Lys Ser Lys Gly Gln Leu Ile
             30                  35                  40
```

| | | | | | | | | | | | | | | | | |
|---|---|---|---|---|---|---|---|---|---|---|---|---|---|---|---|---|
| GTT | GGT | GTT | AAA | AAT | GAT | GTT | CCG | CAT | TAT | GCT | TTA | CTT | GAT | CAA | GCA | 195 |
| Val | Gly | Val | Lys<br>45 | Asn | Asp | Val | Pro | His<br>50 | Tyr | Ala | Leu | Leu | Asp | Gln<br>55 | Ala | |
| ACA | GGT | GAA | ATT | AAA | GGT | TTC | GAA | GTA | GAT | GTT | GCC | AAA | TTG | CTA | GCT | 243 |
| Thr | Gly | Glu<br>60 | Ile | Lys | Gly | Phe | Glu<br>65 | Val | Asp | Val | Ala | Lys<br>70 | Leu | Leu | Ala | |
| AAA | AGT | ATA | TTG | GGT | GAT | GAT | AAA | AAA | ATA | AAA | CTA | GTT | GCA | GTT | AAT | 291 |
| Lys | Ser<br>75 | Ile | Leu | Gly | Asp | Asp<br>80 | Lys | Lys | Ile | Lys | Leu<br>85 | Val | Ala | Val | Asn | |
| GCT | AAA | ACA | AGA | GGC | CCT | TTG | CTT | GAT | AAT | GGT | AGT | GTA | GAT | GCG | GTG | 339 |
| Ala<br>90 | Lys | Thr | Arg | Gly | Pro<br>95 | Leu | Leu | Asp | Asn | Gly<br>100 | Ser | Val | Asp | Ala | Val<br>105 | |
| ATA | GCA | ACT | TTT | ACT | ATT | ACT | CCA | GAG | AGA | AAA | AGA | ATT | TAT | AAT | TTC | 387 |
| Ile | Ala | Thr | Phe | Thr<br>110 | Ile | Thr | Pro | Glu | Arg<br>115 | Lys | Arg | Ile | Tyr | Asn<br>120 | Phe | |
| TCA | GAG | CCT | TAT | TAT | CAA | GAT | GCT | ATA | GGG | CTT | TTG | GTT | TTA | AAA | GAA | 435 |
| Ser | Glu | Pro | Tyr<br>125 | Tyr | Gln | Asp | Ala | Ile<br>130 | Gly | Leu | Leu | Val | Leu<br>135 | Lys | Glu | |
| AAA | AAA | TAT | AAA | TCT | TTA | GCT | GAT | ATG | AAA | GGT | GCA | AAT | ATT | GGA | GTG | 483 |
| Lys | Lys | Tyr<br>140 | Lys | Ser | Leu | Ala | Asp<br>145 | Met | Lys | Gly | Ala | Asn<br>150 | Ile | Gly | Val | |
| GCT | CAA | GCT | GCA | ACT | ACA | AAA | AAA | GCT | ATA | GGT | GAA | GCT | GCT | AAA | AAA | 531 |
| Ala | Gln<br>155 | Ala | Ala | Thr | Thr | Lys<br>160 | Lys | Ala | Ile | Gly | Glu<br>165 | Ala | Ala | Lys | Lys | |
| ATT | GGC | ATT | GAT | GTT | AAA | TTT | AGT | GAA | TTT | CCT | GAT | TAT | CCA | AGT | ATA | 579 |
| Ile<br>170 | Gly | Ile | Asp | Val | Lys<br>175 | Phe | Ser | Glu | Phe | Pro<br>180 | Asp | Tyr | Pro | Ser | Ile<br>185 | |
| AAA | GCT | GCT | TTA | GAT | GCT | AAA | AGA | GTT | GAT | GCG | TTT | TCT | GTA | GAC | AAA | 627 |
| Lys | Ala | Ala | Leu | Asp<br>190 | Ala | Lys | Arg | Val | Asp<br>195 | Ala | Phe | Ser | Val | Asp<br>200 | Lys | |
| TCA | ATA | TTG | TTA | GGT | TAT | GTG | GAT | GAT | AAA | AGT | GAA | ATT | TTG | CCA | GAT | 675 |
| Ser | Ile | Leu | Leu<br>205 | Gly | Tyr | Val | Asp | Asp<br>210 | Lys | Ser | Glu | Ile | Leu<br>215 | Pro | Asp | |
| AGT | TTT | GAA | CCA | CAA | AGT | TAT | GGT | ATT | GTA | ACC | AAA | AAA | GAT | GAT | CCA | 723 |
| Ser | Phe | Glu<br>220 | Pro | Gln | Ser | Tyr | Gly<br>225 | Ile | Val | Thr | Lys | Lys<br>230 | Asp | Asp | Pro | |
| GCT | TTT | GCA | AAA | TAT | GTT | GAT | GAT | TTT | GTA | AAA | GAA | CAT | AAA | AAT | GAA | 771 |
| Ala | Phe<br>235 | Ala | Lys | Tyr | Val | Asp<br>240 | Asp | Phe | Val | Lys | Glu<br>245 | His | Lys | Asn | Glu | |
| ATT | GAT | GCT | TTA | GCG | AAA | AAA | TGG | GGT | TTA | TAAT | | | | | | 805 |
| Ile<br>250 | Asp | Ala | Leu | Ala | Lys<br>255 | Lys | Trp | Gly | Leu | | | | | | | |

(2) INFORMATION FOR SEQ ID NO:8:

(i) SEQUENCE CHARACTERISTICS:
        (A) LENGTH: 259 amino acids
        (B) TYPE: amino acid
        (D) TOPOLOGY: linear (ii) MOLECULE TYPE: protein (xi) SEQUENCE DESCRIPTION: SEQ ID NO:8:

| | | | | | | | | | | | | | | | |
|---|---|---|---|---|---|---|---|---|---|---|---|---|---|---|---|
| Met<br>1 | Val | Phe | Arg | Lys<br>5 | Ser | Leu | Leu | Lys | Leu<br>10 | Ala | Val | Phe | Ala | Leu<br>15 | Gly |
| Ala | Cys | Val | Ala<br>20 | Phe | Ser | Asn | Ala | Asn<br>25 | Ala | Ala | Glu | Gly | Lys<br>30 | Leu | Glu |
| Ser | Ile | Lys<br>35 | Ser | Lys | Gly | Gln | Leu<br>40 | Ile | Val | Gly | Val | Lys<br>45 | Asn | Asp | Val |
| Pro | His<br>50 | Tyr | Ala | Leu | Leu | Asp<br>55 | Gln | Ala | Thr | Gly | Glu<br>60 | Ile | Lys | Gly | Phe |

-continued

| | | | | | | | | | | | | | | |
|---|---|---|---|---|---|---|---|---|---|---|---|---|---|---|
|Glu|Val|Asp|Val|Ala|Lys|Leu|Leu|Ala|Lys|Ser|Ile|Leu|Gly|Asp|Asp|
|65| | | | |70| | | |75| | | | |80|

Lys Lys Ile Lys Leu Val Ala Val Asn Ala Lys Thr Arg Gly Pro Leu
                85                      90                      95

Leu Asp Asn Gly Ser Val Asp Ala Val Ile Ala Thr Phe Thr Ile Thr
            100                     105                     110

Pro Glu Arg Lys Arg Ile Tyr Asn Phe Ser Glu Pro Tyr Tyr Gln Asp
        115                     120                 125

Ala Ile Gly Leu Leu Val Leu Lys Glu Lys Lys Tyr Lys Ser Leu Ala
    130                     135                 140

Asp Met Lys Gly Ala Asn Ile Gly Val Ala Gln Ala Ala Thr Thr Lys
145                 150                     155                 160

Lys Ala Ile Gly Glu Ala Ala Lys Lys Ile Gly Ile Asp Val Lys Phe
                165                     170                 175

Ser Glu Phe Pro Asp Tyr Pro Ser Ile Lys Ala Ala Leu Asp Ala Lys
            180                 185                 190

Arg Val Asp Ala Phe Ser Val Asp Lys Ser Ile Leu Leu Gly Tyr Val
        195                 200                 205

Asp Asp Lys Ser Glu Ile Leu Pro Asp Ser Phe Glu Pro Gln Ser Tyr
    210                     215                 220

Gly Ile Val Thr Lys Lys Asp Asp Pro Ala Phe Ala Lys Tyr Val Asp
225                 230                 235                 240

Asp Phe Val Lys Glu His Lys Asn Glu Ile Asp Ala Leu Ala Lys Lys
                245                     250                 255

Trp Gly Leu ( 2 ) INFORMATION FOR SEQ ID NO:9:

( i ) SEQUENCE CHARACTERISTICS:
          ( A ) LENGTH: 155 base pairs
          ( B ) TYPE: nucleic acid
          ( C ) STRANDEDNESS: double
          ( D ) TOPOLOGY: circular ( i x ) FEATURE:
          ( A ) NAME/KEY: CDS
          ( B ) LOCATION: 5..154

( x i ) SEQUENCE DESCRIPTION: SEQ ID NO:9:

```
TAAT ATG AAT GAA AGT GTA GGT TTT GTT GAA CAT TTA AGA CAA ATT CTT      49
     Met Asn Glu Ser Val Gly Phe Val Glu His Leu Arg Gln Ile Leu
      1               5                  10                  15

ACT TCT TGG GGT TTA TAT GAT GAA AAT AGT ATA AGC CCT TTT GCG GTA       97
Thr Ser Trp Gly Leu Tyr Asp Glu Asn Ser Ile Ser Pro Phe Ala Val
             20                  25                  30

TGG AAA TTT TTA GAT GCT TTG GAT AAT AAA GAT GCT TTT ATT AAT GGT     145
Trp Lys Phe Leu Asp Ala Leu Asp Asn Lys Asp Ala Phe Ile Asn Gly
             35                  40                  45

TTT ATT TAT G                                                       155
Phe Ile Tyr
         50
```

( 2 ) INFORMATION FOR SEQ ID NO:10:

( i ) SEQUENCE CHARACTERISTICS:
          ( A ) LENGTH: 50 amino acids
          ( B ) TYPE: amino acid
          ( D ) TOPOLOGY: linear ( i i ) MOLECULE TYPE: protein ( x i ) SEQUENCE DESCRIPTION: SEQ ID NO:10:

```
Met  Asn  Glu  Ser  Val  Gly  Phe  Val  Glu  His  Leu  Arg  Gln  Ile  Leu  Thr
 1              5                        10                        15

Ser  Trp  Gly  Leu  Tyr  Asp  Glu  Asn  Ser  Ile  Ser  Pro  Phe  Ala  Val  Trp
              20                        25                        30

Lys  Phe  Leu  Asp  Ala  Leu  Asp  Asn  Lys  Asp  Ala  Phe  Ile  Asn  Gly  Phe
              35                        40                        45

Ile  Tyr
     50
```

( 2 ) INFORMATION FOR SEQ ID NO:11:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: protein ( i x ) FEATURE:
        ( A ) NAME/KEY: CDS
        ( B ) LOCATION: 1..60

( x i ) SEQUENCE DESCRIPTION: SEQ ID NO:11:

```
Gly  Glu  Gly  Lys  Leu  Glu  Ser  Ile  Lys  Ser  Lys  Gly  Gln  Leu  Ile  Val
 1              5                        10                        15

Gly  Val  Lys  Asn
              20
```

CAMPYLOBACTER JEJUNI ANTIGENS AND METHODS FOR THEIR PRODUCTION AND USE

RELATED APPLICATION

This application is a Continuation of U.S. patent application Ser. No. 08/114,420, filed Aug. 30, 1993, now abandoned, which is in turn a Continuation-in-part of U.S. patent application Ser. No. 08/112,387, filed Aug. 27, 1993, now abandoned.

FIELD OF THE INVENTION

This invention relates to the *Campylobacter jejuni* antigen PEB1A, to nucleic acid encoding the antigen, to various methods of detecting *Campylobacter jejuni* infection, and to vaccines and treatments for *Campylobacter jejuni* enteritis. In particular, the interaction of the PEB1A antigen with its receptor can be beneficially controlled by a number of techniques described herein.

BACKGROUND OF THE INVENTION

*Campylobacter jejuni* is now recognized as one of the leading causes of diarrheal diseases worldwide. Approximately two million cases of *C. jejuni* enteritis occur in the United States each year, and the actual incidence may be even higher for at least two reasons. First, *C. jejuni* is a fastidious bacterium which requires microaerobic environment (5% $O_2$, 3–10% $CO_2$) to grow, a condition that is not available in many clinical microbiology laboratories. Second, treatment of diarrheal patients with antibiotics for any reason may kill *C. jejuni*, thus causing conventional diagnostic methods based on culturing viable bacteria to yield false negative results. Thus, a new diagnostic technique is needed to detect *C. jejuni* bacteria, whether viable or not.

PEB1A is conserved in all clinical isolates of C. jejuni. Theoretically, it is possible to diagnose C. jejuni infection by detecting the common PEB1A structure in fecal specimens using immunological methods such as ELISA and Western blot but sensitivity may be low because PEB1A is only a minor component of the bacteria. Alternatively, use of PEB1A as antigen to detect specific antibodies for diagnosis of *C. jejuni* infection, while promising, has limitations caused by difficulty in obtaining large quantities of enough purified PEB1A. Thus, more efficient production of PEB1A is desirable.

Prior art attempts at vaccines and therapy for *C. jejuni* enteritis have suffered from incomplete knowledge of the important antigen and receptor interactions discussed herein regarding PEB1A.

SUMMARY OF THE INVENTION

It is therefore an object of the present invention to provide for efficient recombinant production of the PEB1A antigen.

It is another object of the invention to provide an isolated nucleotide, one coding region of which encodes the PEB1A in large quantities, and to provide antibodies thereto, particularly monoclonal antibodies.

It is another object to provide methods and kits for detecting *C. jejuni* infection.

It is another object to provide novel vaccines for *C. jejuni* infection.

It is another object to provide improved treatments for *C. jejuni* enteritis.

It is another object to provide materials for practicing the foregoing methods and treatments.

It is a further object to provide nucleic acid encoding a novel leader sequence for better export of a recombinantly produced protein into the extracellular compartment (e.g., the culture media). This leader sequence may be useful, for example, as part of a fusion protein for expression of a large number of polypeptides. The leader is often cleaved during transport through the cell membrane, advantageously not requiring a further cleavage step by the technician.

The foregoing and other objects are achieved by practice of the inventions described herein.

In one embodiment, the invention provides an isolated nucleic acid encoding a PEB1A antigen, Campylobacter jejuni or antigenic fragment thereof. In preferred embodiments, the nucleic acid comprises nucleotides 25 through 904 shown in SEQ. ID NO: 7, described infra. Expression vectors and hosts for expressing the peptide products of the foregoing nucleic acid are also contemplated.

In another embodiment, the invention provides purified antigenic polypeptide fragments encoded by a portion of the foregoing nucleic acid. In preferred embodiments, the polypeptide consists essentially of amino acids 27 through 259 shown in SEQ. ID NO: 8, described infra.

In another aspect, the invention provides purified antibodies specifically reactive with a polypeptide encoded by the foregoing nucleic acid. In preferred embodiments, they are monoclonal antibodies.

In another aspect of the invention, a method is provided for detecting the presence of *Campylobacter jejuni* infection comprising contacting an antibody-containing sample obtained from a patient suspect of infection, with a detectable amount of an antigenic polypeptide fragment encoded by the nucleic acid discussed above. Following a sufficient time to allow formation of a complex between the polypeptide and any anti-*Campylobacter jejuni* antibodies present in the sample, formation of complex is measured by standard techniques. In preferred embodiments, any detected formation of complex is then compared to a predetermined positive threshold value, and considered a positive reading only if it exceeds that predetermined value. The volume will vary depending upon the detection means chosen, the concentration and amount of protein contacted with the sample, and other parameters known in the art. The preferred positive threshold value may be defined generically as a value greater than the mean plus one interval of standard deviation from the results observed from a negative control group, all other parameters (dilution of sample, time of incubation, etc.) being held constant. In some embodiments where higher specificity is desired, mean plus two or mean plus three standard deviations may be utilized. The negative control group should consist of asymptomatic individuals who are members of the population which is unlikely to include individuals infected with *C. jejuni*. A preferred control group, for example, is a group of asymptomatic U.S. children below ten years of age. Such children form a population unlikely to be infected.

In an alternative method of detecting the presence of *Campylobacter jejuni*, a sample is obtained from a patient suspected of infection and is contacted with a detectable amount of antibodies to PEB1A (or other antigenic protein encoded by the nucleic acid discussed above). The remainder of this alternative method is analogous to the detection method described above (for detecting anti-*C. jejuni* antibodies in a sample), i.e, antibodies/antigen complex is measured, and preferably is then compared to a predetermined positive threshold value determined as described above.

Yet another method of detecting *C. jejuni* infection in accordance with the invention comprises a direct test for the characteristic nucleic acid described herein which encodes PEB1A. Numerous techniques (e.g., hybridization of nucleic acids in the sample with a known nucleic acid, selective amplification of a nucleic acid encoding PEB1A, etc.) are described in detail infra.

The invention also provides several different techniques for treating *C. jejuni* enteritis in a patient in need of such treatment. In one aspect, a ligand specifically reactive with the PEB1A antigen is administered.

In another method of treatment, a ligand or antagonist of a receptor for the PEB1A antigen is administered.

Pharmaceutical compositions for carrying out the methods of treatment of the invention are also provided, as are kits for carrying out the diagnostic methods.

In another embodiment, the invention provides a leader sequence consisting essentially of amino acids 1 through 26 shown in SEQ. ID NO: 8. This leader sequence is encoded by the first 78 nucleotides 25–102 shown in SEQ. ID NO: 7. It has been discovered that nucleic acid encoding this leader sequence may have a broad range of application with expression vectors in other systems and for expressing other proteins. In particular, the leader is especially effective in exporting proteins across the outer membrane, and also has the advantage of being cleaved in the process of transport, thus avoiding a subsequent cleavage step. This leader is useful in systems expressing the PEB1A peptide of the invention and for expressing other peptides as part of a fusion protein with said leader.

In another embodiment, the invention provides a mutant form of *C. jejuni* useful in vaccines. The mutant form has been genetically engineered not to express PEB1A. Without intending to be bound by theory, it is believed that such a mutant form may provoke an immune response while not itself causing *C. jejuni* enteritis, the mutation making it difficult for the organism to bind the PEB1A receptor.

Other features and advantages of the present invention will become apparent from the following description of the invention which refers to the accompanying drawings, nucleotide sequences and amino acid sequences.

BRIEF DESCRIPTION OF THE DNA AND AMINO ACID SEQUENCES

The nucleotide and the deduced amino acid sequences of a 2687bp pPB119 fragment (hereinafter referred to as the pPB119 composite) includes 5 open reading frames designated sequentially "A"–"E" (appearing in SEQ. ID. NOS: 1, 3, 5, 7 and 9, respectively). It contains a coding region for peb 1A, generally open reading frame "D" (appearing SEQ. ID. NO: 7). Each of SEQ. ID. NOS: 1, 3, 5, 7 and 9 include upstream and downstream "non-coding" regions which, as described below, overlap since, in nature, each of SEQ. ID. NOS: 1, 3, 5, 7 and 9 are located sequentially on a single composite strand of DNA. Nucleotides are numbered on the right of each line and amino acids for each open reading frame (ORF) are numbered under every fifth amino acid. The ribosome binding sites (S.D.) and putative transcriptional promoters and terminators (e.g. inverted repeat sequences that may indicate transcriptional terminators) are as indicated below. The upstream non-coding regions of SEQ. ID. NOS: 3, 5, 7 and 9 include the stop codon of the prior coding region. The amino acid sequence of SEQ. ID. NO: 11 was determined by amino terminal sequencing of mature PEB1A from C. jejuni, and as discussed below, was shown to substantially match the sequence predicted by a portion of the nucleotide sequence shown in SEQ. ID. NO: 7.

SEQ. ID. NO: 1 is the nucleotide sequence for a portion of the pPB119 composite corresponding to its partial ORF A and comprises nucleotides 2 through 64. Nucleotides 65 through 82 comprise a non-coding region downstream of the nucleotide of ORF A. Nucleotides 65 through 82 include the stop codon (at 65–67) and correspond to the upstream non-coding region of SEQ. ID. NO: 3.

SEQ. ID. NO: 2 is the deduced amino acid sequence of the nucleotide of SEQ. ID. NO:1.

SEQ. ID. NO: 3 is the nucleotide sequence for a portion of the pPB119 composite corresponding to its ORF B and comprises nucleotides 19 through 810. Nucleotides 1 through 18 comprise a non-coding region upstream of the coding region of ORF B and correspond to the non-coding region downstream of the coding region of ORF A (SEQ. ID. NO: 1). Nucleotides 8–11 code for the ribosome binding site (S.D.). Nucleotides 811 through 941 comprise a non-coding region downstream of ORF B (811–813 being the stop codon). A putative transcriptional terminator appears at nucleotides 817 through 851.

SEQ. ID. NO: 4 is the deduced amino acid sequence of the nucleotide of SEQ. ID. NO: 3.

SEQ. ID. NO: 5 is the nucleotide sequence for a portion of the pPB119 composite corresponding to its ORF C and comprises nucleotides 132 through 857. Nucleotides 1 through 131 comprise a non-coding region upstream of the nucleotide of ORF C and correspond to the non-coding region downstream of the coding region of ORF B (SEQ. ID. NO: 3). This region includes a putative promoter at nucleotides 56–87, and an S.D. at 122–125. Nucleotides 858 through 881 comprise a non-coding region downstream of the nucleotide of ORF C (858–860 being a stop codon).

SEQ. ID. NO: 6 is the deduced amino acid sequence of the nucleotide of SEQ. ID. NO: 5.

SEQ. ID. NO: 7 is the nucleotide sequence for a portion of the pPB119 composite corresponding to its ORF D and comprises nucleotides 25 through 801. Nucleotides 1 through 24 comprise a non-coding region upstream of the coding region of ORF D and correspond to the non-coding region downstream of the coding region of ORF C (SEQ. ID. NO: 5). It has an S.D. at 15–18. Nucleotides 802 through 804 form a stop codon.

SEQ. ID. NO: 8 is the deduced amino acid sequence of the nucleotide of SEQ. ID. NO: 7.

SEQ. ID. NO: 9 is the nucleotide sequence for a portion of the pPB119 composite corresponding to its partial ORF E and comprises nucleotides 5 through 154. Nucleotides 1 through 4 comprise a non-coding region upstream of the nucleotide of ORF E and correspond to stop codon and one additional bp downstream of the coding region of ORF D (SEQ. ID. NO: 7).

SEQ. ID. NO: 10 is the deduced amino acid sequence of the nucleotide of SEQ. ID. NO: 9.

SEQ. ID. NO: 11 is an amino acid sequence determined by amino terminal sequencing of actual mature PEB1A protein from *C. jejuni* and closely corresponds with deduced amino acids 27 through 46 of SEQ. ID. NOS. 7 and 8.

BRIEF DESCRIPTION OF THE DRAWING(S)

FIG. 1 is an immunoblot of lysates of lysogenized *E. coli* Y1089 producing recombinant *C. jejuni* antigens. Lanes are: (a) cells of *C. jejuni* strain 81-176; (b) cells of *E. coli* strain Y1089 containing λgt11 without an insert; (c) cells of lysogenic clone 1; (d) cells of lysogenic clone 2. *E. coli* cells in lanes b, c, and d were cultured overnight in the presence of 2 µM IPTG to induce expression of genes downstream to the lacZ promoter in λgt11. A band migrating at approximately 28 kDa (indicated by arrow) was recognized by rabbit antiserum to the purified PEB1A (1:10,000) in clones 1 and 2 but not in the strain harboring λgt11 alone.

FIG. 2 is a restriction map of pPB119 showing a sequencing strategy for the peb1A gene. Restriction sites are shown above the 2.6 kb insert with single letter E (EcoRI), H (HindIII), and N (NcoI). Three complete open reading frames (ORFs), B, C, D, and two partial ORFs, A and E, are indicated below the insert. The large arrow represents the direction of transcription of peb1A. pPB203 and pPB11 are deletion mutants of pPB119. Solid arrows represent sequences obtained from deletion mutants, and dotted arrows from primer sequencing.

FIG. 3 shows a southern hybridization illustrating the conservation of peb1A gene in C. jejuni chromosomal DNA digested with HindIII. A 702 bp PCR product corresponding to the DNA sequence of mature PEB1A was used as probe. Lanes are C. jejuni strains 81–176 (a), 85-H (b), and 81-95 (c); C. coli strains D126 (d) and D730 (e); and C. fetus strains 23D (f) and 84–91 (g). Molecular weight markers (kb) are shown at left.

FIG. 4A is a PCR amplification of 702 bp peb1A fragment from Campylobacter strains. Lanes are: C. jejuni strains 81–176 (a), D1916 (b), 85AC (c); C. coli strains D126 (d), and D1035 (e); C. lari strains D110 (f), and D67 (g); C. fetus strain 23D (h); E. coli with pPB119 (i). A 702 bp amplified PCR product was found in all C. jejuni strains (arrow) but not in the other Campylobacter species.

FIG. 4B is a restriction pattern of 702 bp PCR products from C. jejuni strains. The 702 bp PCR products were undigested or were digested with SspI or HaeIII. Strains used as templates are: 81–176 (lane a), D1916 (lane b), 85AC (lane c) and E. coli pPB119 (lane d). SspI cleaved the 702 bp PCR products from each strain into 370, 173 and 159 bp fragments and HaeIII cleaved the PCR products from each strain into 499 and 203 bp fragments, indicating that the peb1A gene is highly conserved in C. jejuni.

FIG. 5 is a restriction map of pPB119:km used in construction of a PEB1A⁻ mutant. The km cassette from pILL600 was ligated into the NheI site of pPB119 to create pPB119:km. Restriction sites are E, EcoRI; H, HindIII. The location of the 702 bp PEB1A probe is also shown.

FIG. 6 is an SDS-PAGE and Western blot of wild-type and PEB1A⁻ mutant strains. Panels are: SDS-PAGE of (a) whole cells or (b) glycine extract of C. jejuni, and (c) Western blot of whole cells of C. jejuni with rabbit-anti-PEB1A. Lanes are: (W) wild type C. jejuni strain 81-176; (M) PEB1A⁻ mutant strain. Molecular mass markers(in kilodaltons) are shown at left. Arrow indicates the position of PEB1A band.

FIG. 7 illustrates export of PEB1A into culture supernatants by pPB203 as examined by SDS-PAGE with 12% acrylamide. E. coli strain XL1-Blue harboring either vector (pUC19) alone, pPB119, or its deletion mutant pPB203 were cultured in the absence (−) or presence (+) of 2 µM IPTG to induce expression of PEB1A protein. Bacterial cells (C) were separated from culture supernatants (S) by centrifugation. Expression of PEB1A in pPB119 was cell-associated and increased by IPTG induction. pPB203, a deletion mutant in which the 1.0 kb EcoRI-HindIII fragment was deleted from the parental plasmid pPB119, produced several-fold more PEB1A than pPB119 and exported PEB1A into the culture supernatant with greater than 70% purity as shown by the arrow.

DETAILED DESCRIPTION OF THE INVENTION

Nucleic Acids

Figure 1:
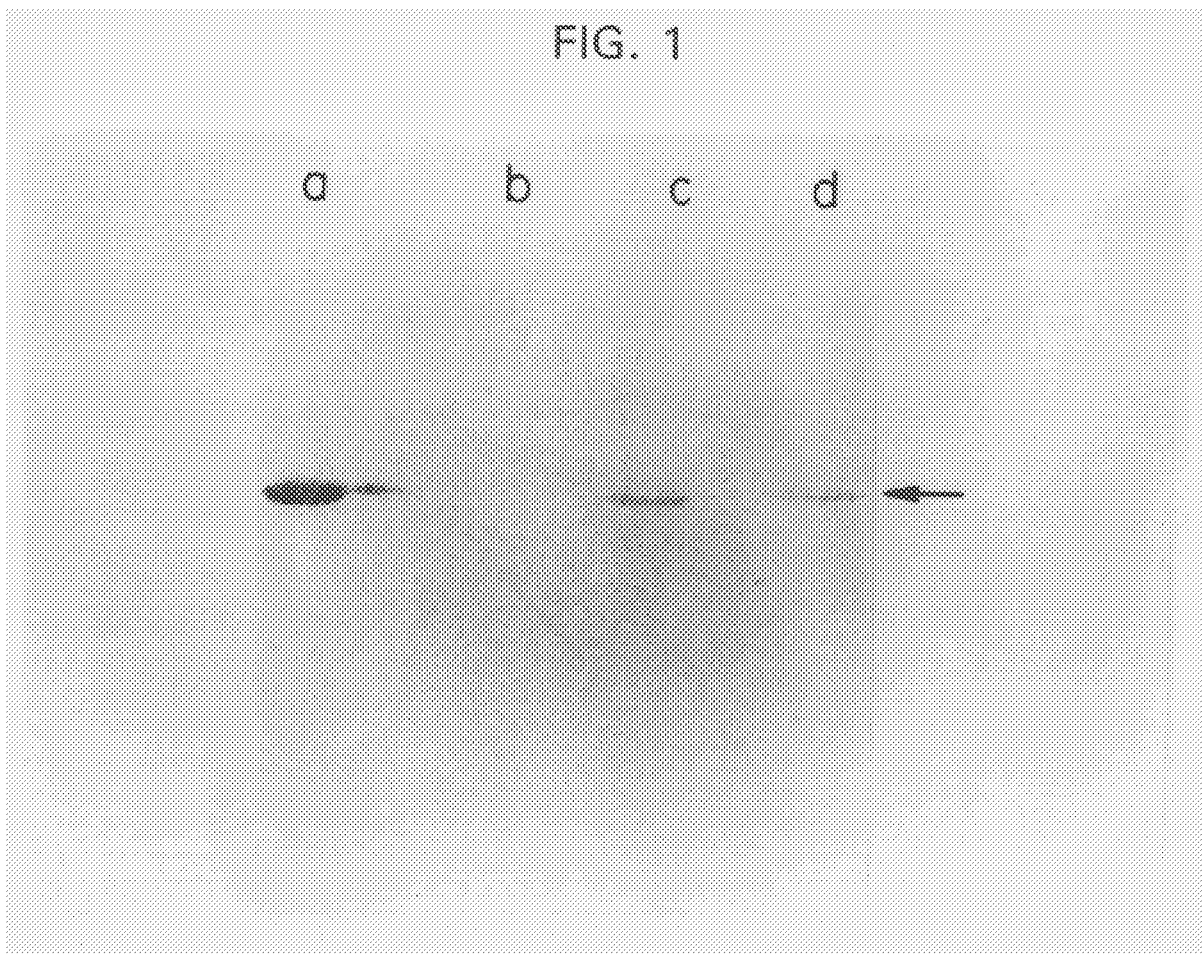

The present invention provides an isolated nucleic acid encoding an approximately 25.5 kDa PEB1A antigen or fragment of C. jejuni. The "isolated" nucleic acid is separated from other nucleic acids found in the naturally occurring organism. The nucleic acid encoding the PEB1A is specific for C. jejuni expressing the PEB1A, and does not hybridize with other nucleic acids sufficiently to prevent adequate positive hybridization with PEB1A-encoding nucleic acids from C. jejuni. Specifically, an example of such a nucleic acid is a open reading frame of 780 base pairs comprising nucleotides 25 through 804 of SEQ ID NO: 7. This specific nucleic acid can be used to detect C. jejuni possessing PEB1A antigen in methods such as polymerase chain reaction, ligase chain reaction and hybridization.

The 2687 base pair sequence (the pPB119 composite) or appropriate fragments thereof can be utilized to produce a PEB1A protein, by splicing into an appropriate vector and transfecting an appropriate host.

In addition, the nucleic acid can be homologous with nucleotide sequences present in other bacteria. Such an amino acid sequence shared with other bacteria can be used for example to simultaneously detect related strains or as a basis for a multiprotective vaccine.

An isolated nucleic acid capable of selectively hybridizing with or selectively amplifying a nucleic acid encoding the PEB1A antigen or fragments thereof is also contemplated. An isolated nucleic acid complementary to the above nucleic acid is also provided. The sequences can be selected based on the nucleotide sequence and the utility of the particular sequence.

Modifications to the nucleic acids of the invention are also contemplated as long as the essential structure and function of the polypeptide encoded by the nucleic acids is maintained. Likewise, fragments used as primers or probes can have substitutions so long as enough complementary bases exist for selective hybridization. (See e.g., Kunkel et al. Methods Enzymol. 1987:154:367).

Antigen

Purified antigenic polypeptide fragments encoded by the nucleic acids of the present invention are also contemplated. The "purified" antigen is sufficiently free of contaminants or cell components with which the antigen normally occurs to distinguish the antigen from the contaminants or components. The purified PEB1A antigen and antigenic fragments thereof are referred to herein as "the antigen".

Specifically, a 25.5 kDa antigenic polypeptide is encoded by an open reading frame of 780 bases within the 2687 base pair cloned insert, consisting essentially of the amino acids encoded by nucleotides 25 through 804 contained in the nucleotide sequence defined in the Sequence Listing as SEQ ID NO: 7.

An antigenic fragment of the antigen can be isolated from the whole antigen by chemical or mechanical disruption. The purified fragments thus obtained can be tested to determine their antigenicity and specificity by the methods taught herein. Antigenic fragments of the antigen can also be synthesized directly. An immunoreactive fragment is an amino acid sequence of at least about 5 consecutive amino acids derived from the PEB1A antigen.

The polypeptide fragments of the present invention can also be recombinant proteins obtained by cloning nucleic acids encoding the polypeptide in an expression system capable of producing the antigenic polypeptide or fragments thereof.

Once the amino acid sequence of the antigen is provided, it is also possible to synthesize, using standard peptide synthesis techniques, peptide fragments chosen to be homologous to immunoreactive regions of the antigen and to modify these fragments by inclusion, deletion or modification of particular amino acids residues in the derived sequences. Thus, synthesis or purification of an extremely large number of peptides derived from the antigen is possible.

The amino acid sequences of the present polypeptides can contain an immunoreactive portion of PEB1A antigen attached to sequences designed to provide for some additional property, such as solubility. The amino acid sequences of an PEB1A antigen can include sequences in which one or more amino acids have been substituted with another amino acid to provide for some additional property, such as to remove/add amino acids capable of disulfide bonding, to increase its bio-longevity, alter enzymatic activity, or alter interactions with gastric acidity. In any case, the peptide must posses a bioactive property, such as immunoreactivity, immunogenicity, etc.

Determining Immunogenicity

The purified polypeptide fragments thus obtained can be tested to determine their immunogenicity and specificity by techniques known in the art. Various concentrations of a putative immunogenically specific fragment are prepared and administered to an animal and the immunological response (e.g., the production of antibodies or cell mediated immunity) of an animal to each concentration is determined. The amounts of antigen administered depend on the subject e.g. a human or a guinea pig, the condition of the subject, the size of the subject, etc. Thereafter an animal so inoculated with the antigen can be exposed to the bacterium to test the potential vaccine effect of the specific immunogenic fragment. The specificity of a putative immunogenic fragment can be ascertained by testing sera, other fluids or lymphocytes from the inoculated animal for cross reactivity with other closely related bacteria.

Vectors and Hosts

A vector comprising the nucleic acids of the present invention is also provided. The vectors of the invention can be in a host capable of expressing the antigen.

There are numerous *E. coli* expression vectors known to one of ordinary skill in the art useful for the expression of the antigen. Other microbial hosts suitable for use include bacilli, such as *Bacillus subtilus*, and other enterobacteriaceae, such as Salmonella, Serratia, and various Pseudomonas species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences for example, for initiating and completing transcription and translation. If necessary an amino terminal methionine can be provided by insertion of a Met codon 5' and in-frame with the antigen. Also, the carboxyl-terminal extension of the antigen can be removed using standard oligonucleotide mutagenesis procedures.

Additionally, yeast expression can be used. There are several advantages to yeast expression systems. First, evidence exists that proteins produced in a yeast secretion systems exhibit correct disulfide pairing. Second, posttranslational glycosylation is efficiently carried out by yeast secretory systems. The Saccharomyces cerevisiae pre-pro-alpha-factor leader region (encoded by the MF$\alpha$-1 gene) is routinely used to direct protein secretion from yeast (Brake et al., 1984). The leader region of pre-pro-alpha-factor contains a signal peptide and a pro-segment which includes a recognition sequence for a yeast protease encoded by the KEX2 gene: this enzyme cleaves the precursor protein on the carboxyl side of a Lys-Arg dipeptide cleavage-signal sequence. The antigen coding sequence can be fused in-frame to the pre-pro-alpha-factor leader region. This construct is then put under the control of a strong transcription promoter, such as the alcohol dehydrogenase I promoter or a glycolytic promoter. The antigen coding sequence is followed by a translation termination codon which is followed by transcription termination signals. Alternatively, the antigen coding sequences can be fused to a second protein coding sequence, such as Sj26 or $\beta$-galactosidase, used to facilitate purification of the fusion protein by affinity chromatography. The insertion of protease cleavage sites to separate the components of the fusion protein is applicable to constructs used for expression in yeast.

Mammalian cells permit the expression of proteins in an environment that favors important posttranslational modifications such as folding and cysteine pairing, addition of complex carbohydrate structures, and secretion of active protein. Vectors useful for the expression of antigen in mammalian cells are characterized by insertion of the antigen coding sequence between a strong viral promoter and a polyadenylation signal. The vectors can contain genes conferring either gentamicin or methotrexate resistance for use as selectable markers. The antigen and immunoreactive fragment coding sequence can be introduced into a Chinese hamster ovary cell line using a methotrexate resistance-encoding vector. Presence of the vector DNA in transformed cells can be confirmed by Southern analysis and production of an RNA corresponding to the antigen coding sequence can be confirmed by Northern analysis. A number of other suitable host cell lines capable of secreting intact human proteins have been developed in the art, and include the CHO cell lines, HeLa cells, myeloma cell lines, Jurkat cells, etc. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoflogulin genes, SV40, Adenovirus, and Bovine Papilloma Virus, etc. The vectors containing the DNA segments of interest can be transferred into the host cell by well-known methods, which vary depending on the type of cellular host. For example, calcium chloride transfection is commonly utilized for prokaryotic cells, whereas calcium phosphate treatment or electroporation may be used for other cellular hosts.

Materials and methods for baculovirus/insect cell expression systems are commercially available in kit form from, inter alia, Invitrogen, San Diego, Calif. ("MaxBac" kit). These techniques are generally known to those skilled in the art and fully described in Summers and Smith, *Texas Agricultural Experiment Station Bulletin No.* 1555 (1987) (hereinafter "Summers and Smith").

Recombinant baculovirus expression vectors have been developed for infection into several insect cells. For example, recombinant baculoviruses have been developed for, inter alia, *Aedes aegypti, Autographa Californica, Bombyx mori, Drosophila melanogaster, Spodoptera frugiperda*, and *Trichoplusia ni* (PCT Pub. No. WO 89/046699; Carbonell et al., *J. Virol.*, 56:153 (1985); Wright, *Nature*, 321:718 (1986); Smith et al., *Mol. Cell. Biol.*, 3:2156 (1983), and see generally, Fraser, et al., *In vitro Cell. Dev. Biol.*, 25:225 (1989).

Alternative vectors for the expression of antigen in mammalian cells can also be employed, e.g those similar to those developed for the expression of human gamma-interferon, tissue plasminogen activator, clotting Factor VIII, hepatitis B virus surface antigen, protease Nexinl, and eosinophil major basic protein. Further, the vector can include CMV promoter sequences and a polydenylation signal available for expression of inserted DNAs in mammalian cells (such as COS7).

The DNA sequences can be expressed in hosts after the sequences have been operably linked to, i.e., positioned to ensure the functioning of, an expression control sequence. These expression vectors are typically replicable in the host organisms either as episomes or as an integral part of the host chromosomal DNA. Commonly, a selectable marker such as genes for tetracycline resistance or hygromycin resistance are utilized to permit detection and/or selection of those cells transformed with the desired DNA sequences (see, e.g., U.S. Pat. No. 4,704,362).

Polynucleotides encoding a variant polypeptide may include sequences that facilitate transcription (expression sequences) and translation of the coding sequences such that the encoded polypeptide product is produced. Construction of such polynucleotides is well known in the art. For example, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector.

Purified Antibodies

A purified monoclonal antibody specifically reactive with PEB1A is also provided. The antibodies can be specifically reactive with a unique epitope of PEB1A or they can also react with epitopes of other organisms. The term "reactive" means capable of binding or otherwise associating nonrandomly with an antigen. "Specifically reactive" as used herein describes an antibody or other ligand that does not cross react substantially with any antigen other than the one specified, in this case, usually PEB1A antigen, or antigenic fragments thereof. Antibodies can be made as described in the Examples (see also, Harlow and Lane, *Antibodies; A Laboratory Manual*, Cold Spring Harbor Laboratory, Cold Spring Harbor, N.Y., 1988). Briefly, purified antigen can be injected into an animal in an amount and in intervals sufficient to elicit an immune response. Antibodies can either be purified directly, or spleen cells can be obtained from the animal. The cells are then fused with an immortal cell line and screened for antibody secretion.

The antibody can be bound to a substrate or labeled with a detectable moiety, or both bound and labeled. The detectable moieties contemplated with the composition of the present invention are those listed below in the description of the diagnostic methods, including fluorescent, enzymatic and radioactive markers.

Antigen Bound to Substrate

A purified PEB1A antigen bound to a substrate and a ligand specifically reactive with the antigen are also contemplated. Such a purified ligand specifically reactive with the antigen can be an antibody. The antibody can be a monoclonal antibody obtained by standard methods and as described herein. The monoclonal antibody can be secreted by a hybridoma cell line specifically produced for that purpose (Harlow and Lane, 1988). Likewise, nonhuman polyclonal antibodies specifically reactive with the antigen are within the scope of the present invention. The polyclonal antibody can also be obtained by the standard immunization and purification protocols (Harlow and Lane, 1988).

Serological Detection (Diagnosis)

Methods Detecting Antibody with the Antigen

The present invention provides a method of detecting the presence of *C. jejuni* strain possessing the PEB1A antigen in a subject, comprising the steps of contacting an antibody-containing sample from the subject with a detectable amount of the PEB1A antigenic fragment of the present invention and detecting the reaction of the fragment and the antibody, the reaction indicating the presence of the *C. jejuni* strain or previous infection with the *C. jejuni* strain.

Detecting Antigen with Antibody/Ligand

One example of the method of detecting *C. jejuni* possessing the PEB1A antigen is performed by contacting a fluid or tissue sample from the subject with an amount of a purified antibody specifically reactive with the antigen, and detecting the reaction of the ligand with the antigen. It is contemplated that the antigen will be on intact cells containing the antigen, or will be fragments of the antigen. As contemplated herein, the antibody includes any ligand which binds the antigen, for example, an intact antibody, a fragment of an antibody or another reagent that has reactivity with the antigen. The fluid sample of this method can comprise any body fluid which would contain the antigen or a cell containing the antigen, such as blood, plasma, serum, saliva and urine. Other possible examples of body fluids include sputum, mucus, gastric juice and the like.

ELISA

Immunofluorescence assays (IFA) and enzyme immunoassays such as enzyme linked immunosorbent assays (ELISA) and immunoblotting can be readily adapted to accomplish the detection of the antigen. An ELISA method effective for the detection of the antigen can, for example, be as follows: (1) bind the antibody to a substrate; (2) contact the bound antibody with a fluid or tissue sample containing the antigen; (3) contact the above with a secondary antibody bound to a detectable moiety (e.g., horseradish peroxidase enzyme or alkaline phosphatase enzyme); (4) contact the above with the substrate for the enzyme; (5) contact the above with a color reagent; (6) observe color change. The above method can be readily modified to detect antibody as well as antigen.

Competitive Inhibition Assay

Another immunologic technique that can be useful in the detection of *C. jejuni* expression PEB1A or previous *C. jejuni* infection utilizes monoclonal antibodies (MAbs) for detection of antibodies specifically reactive with PEB1A antigen. Briefly, sera or other body fluids from the subject is reacted with the antigen bound to a substrate (e.g. an ELISA 96-well plate). Excess sera is thoroughly washed away. A labeled (enzyme-linked, fluorescent, radioactive, etc.) monoclonal antibody is then reacted with the previously reacted antigen-serum antibody complex. The amount of inhibition of monoclonal antibody binding is measured relative to a control (no patient serum antibody). The degree of monoclonal antibody inhibition is a very specific test for a particular variety or strain since it is based on monoclonal antibody binding specificity. MAbs can also be used for detection directly in cells by IFA.

Micro-Agglutination Assay

A micro-aggulatination test can also be used to detect the presence of the *C. jejuni* strain in a subject. Briefly, latex beads (or red blood cells) are coated with the PEB1A and mixed with a sample from the subject, such that antibodies in the tissue or body fluids that are specifically reactive with the antigen crosslink with the antigen, causing agglutination. The agglutinated antigen-antibody complexes form a precipitate, visible with the naked eye or by spectrophotometer. In modification of the above test, antibodies specifically reactive with the antigen can be bound to the beads and antigen in the tissue or body fluid thereby detected.

Sandwich Assay/Flow Cytometry/Immunoprecipitation

In addition, as in a typical sandwich assay, the antibody can be bound to a substrate and reacted with the antigen. Thereafter, a secondary labeled antibody is bound to epitopes not recognized by the first antibody and the secondary antibody is detected. Since the present invention provides PEB1A antigen for the detection of C. jejuni or previous C. jejuni infection, other serological methods such as flow cytometry and immunoprecipitation can also be used as detection methods.

In the diagnostic methods taught herein, the antigen can be bound to a substrate and contacted by a fluid sample such as serum, urine, saliva or gastric juice. This sample can be taken directly from the patient or in a partially purified form. In this manner, antibodies specific for the antigen (the primary antibody) will be specifically react with the bound antigen. Thereafter, a secondary antibody bound to, or labeled with, a detectable moiety can be added to enhance the detection of the primary antibody. Generally, the secondary antibody or other ligand which is reactive, either specifically with a different epitope of the antigen or non-specifically with the ligand or reacted antibody, will be selected for its ability to react with multiple sites on the primary antibody. Thus, for example, several molecules of the secondary antibody can react with each primary antibody, making the primary antibody more detectable.

Detectable Moieties

The detectable moiety will allow visual detection of a precipitate or a color change, visual detection by microscopy, or automated detection by spectrometry, radiometric measurement or the like. Examples of detectable moieties include fluorescein and rhodamine (for fluorescence microscopy), horseradish peroxidase (for either light or electron microscopy and biochemical detection), biotin-streptavidin (for light or electron microscopy) and alkaline phosphatase (for biochemical detection by color change). The detection methods and moieties used can be selected, for example, from a list above or other suitable examples by the standard criteria applied to such selections (Harlow and Lane, 1988).

Treatment Methods

Methods of treating C. jejuni enteritis in a subject using the compositions of the present invention are provided. For example, in one such method an amount of ligand specifically reactive with the PEB1A antigen of C. jejuni sufficient to bind the antigen in the subject and improve the subject's clinical condition is administered to the subject. Such improvement results from the ligand interfering with the antigen's normal function in inducing cell adherence inflammation and cellular damage. The ligand can be purified monoclonal antibody specifically reactive with the antigen, a purified polyclonal antibody derived from a nonhuman animal, or other reagent having specific reactivity with the antigen. Additionally, cytotoxic moieties can be conjugated to the ligand/antibody by standard methods. Examples of cytotoxic moieties include ricin A chain, diphtheria toxin and radioactive isotopes.

Another method of treating C. jejuni enteritis subject comprises administering to the subject an amount of a ligand/antagonist for a receptor for the PEB1A antigen of C. jejuni sufficient to react with the receptor and prevent the binding of the PEB1A antigen to the receptor. The result is an improvement in the subject's clinical condition. Alternatively, the treatment method can include administering to the subject an amount of an analogue of a PEB1A receptor to result in competitive binding of the PEB1A antigen, thus inhibiting binding of the PEB1A antigen to its wild type receptor. The receptor is localized on cells present in the intestinal mucosa, such as epithelial cells, inflammatory cells, or endothelial cells.

Vaccines

The PEB1A antigen of this invention can be used in the construction of a vaccine comprising an immunogenic amount of the antigen and a pharmaceutically acceptable carrier. The vaccine can be the entire antigen, the antigen on an intact C. jejuni, E. coli or other strain. The vaccine can then be used in a method of preventing C. jejuni infection. As mentioned, supra, mutant forms of C. jejuni may also be used.

Immunogenic amounts of the antigen can be determined using standard procedures. Briefly, various concentrations of a putative specific immunoreactive epitope are prepared, administered to an animal and the immunological response (e.g., the production of antibodies) of an animal to each concentration is determined.

The pharmaceutically acceptable carrier in the vaccine of the instant invention can comprise saline or other suitable carriers (Arnon, R. (Ed.) Synthetic Vaccines I:L 83–92, CRC Press, Inc., Boca Raton, Fla., 1987). An adjuvant can also be a part of the carrier of the vaccine, in which case it can be selected by standard criteria based on the antigen used, the mode of administration and the subject (Arnon R. (Ed.), 1987). Methods of administration can be by oral or sublingual means, or by injection, depending on the particular vaccine used and the subject to whom it is administered.

It can be appreciated from the above that the vaccine can be used as a prophylactic (to prevent infection) or a therapeutic (to treat disease after infection) modality. Thus, the invention provides methods of preventing or treating C. jejuni infection and the associated diseases by administering the vaccine to a subject.

Such vaccines comprise antigen or antigens, usually in combination with "pharmaceutically acceptable carriers," which include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as immunostimulating agents ("adjuvants"). Furthermore, the antigen may be conjugated to a bacterial toxoid, such as a toxoid from diphtheria, tetanus, cholera, H. pylori, etc. pathogens.

Preferred adjuvants to enhance effectiveness of the composition include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides, or bacterial cell wall components), such as for example (a) MF59 (PCT Publ. No. WO 90/14837), containing 5% Squalene, 0.5% TWEEN 80 (polyoxyethylene-sorbitan monooleate) and 0.5% SPAN 85 (optionally containing various amounts of MTP-PE, although not required) formulated into submicron particles using a microfluidizer such as Model 110Y microfluidizer (Microfluidics, Newton, Mass.), (b) SAF, containing 10% Squalane, 0.4% TWEEN 80 (polyoxyethylene-sorbitan monooleate), 5% pluronic-blocked polymer L121, and thr-MDP either microfluidized into a submicron emulsion or vortexed to generate a larger particle size emulsion, and (c) RIBI ADJUVANT SYSTEM™ (RAS), (Ribi Immunochem, Hamilton, Mont.) which is a adjuvant containing 2% Squalene, 0.2% TWEEN 80 (polyoxyethylene-sorbitan monooleate), and one or more bacterial cell wall components from the group consisting of monophosphorylipid A (MPL), trehalose dimycolate (TDM), and cell wall skeleton (CWS), preferably DETOX™ (adjuvant containing both monophosphorylipid A and cell wall skeleton); (3) saponin adjuvants, such as STIMULON modified saponins derived from *quillaja saponaria* (Cambridge Bioscience, Worcester, Mass.) may be used or particles generated therefrom such as ( ISCOMs (immunostimulating complexes); (4) Complete Freunds Adjuvant and Incomplete Freunds Adjuvant (IFA); (5) Cytokines, such as interleukins (IL-1, IL-2, etc.), macrophage colony stimulating factor (M-CSF), tumor necrosis factor (TNF), etc.; and (6) other substances that act as immunostimulating agents to enhance the effectiveness of the composition. Alum and MF59 are preferred.

Muramyl peptides include, but are not limited to, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-huydroxyphosphoryloxy)-ethylamine (MTP-PE), etc.

The immunogenic compositions (e.g., the antigen, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect.

Typical immunogenic compositions used as vaccines comprise an immunologically effective amount of antigenic polypeptides, as well as any other of the above-mentioned components, as needed. By "immunologically effective amount," it is meant that the administration of that amount to an individual, either in a single does or as part of a series, is effective for treatment or prevention. This amount varies depending upon the health and physical condition of the individual to be treated, the taxonomic group of individual to be treated (e.g., nonhuman primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials.

The immunogenic compositions are conventionally administered parenterally, e.g., by injection, either subcutaneously or intramuscularly. Additional formulations suitable for other modes of administration include oral and pulmonary formulations, suppositories, and transdermal applications. Dosage treatment may be a single dose schedule or a multiple dose schedule. The vaccine may be administered in conjunction with other immunoregulatory agents.

Nucleic Acid Detection (Diagnosis) Methods

The presence of the PEB1A antigen and *C. jejuni* possessing the PEB1A antigen can also be determined by detecting the presence of a nucleic acid specific for the antigen. The specificity of these sequences for the antigen can be determined by conducting a computerized comparison with known sequences, catalogued in GenBank, a computerized database, using the computer programs Word Search or FASTA of the Genetics Computer Group (Madison, Wisc.), which search the catalogued nucleotide sequences for similarities to the gene in question.

The nucleic acid specific for the antigen can be detected utilizing a nucleic acid amplification technique, such as polymerase chain reaction or ligase chain reaction. Alternatively, the nucleic acid is detected utilizing the direct hybridization or by utilizing a restriction fragment length polymorphism. For example, the present invention provides a method of detecting the presence of *C. jejuni*, possessing the PEB1A antigen, comprising ascertaining the presence of a nucleotide sequence associated with a restriction endonuclease cleavage site. In addition, PCR primers which hybridize only with nucleic acids specific for the antigen can be utilized. The presence of amplification indicates the presence of the antigen. In another embodiment, a restriction fragment of a DNA sample can be sequenced directly using for example, Sanger ddNTp sequencing or 7-deaza-2'-deoxyguanosine 5'-triphosphate and Taq polymerase, and compared to the known unique sequence to detect *C. jejuni*. In a further embodiment, the present invention provides a method of detecting the presence of *C. jejuni* by selective amplification by the methods described above. In yet another embodiment, *C. jejuni* can be detected by directly hybridizing the unique sequence with a PEB1A selective nucleic acid probe. Furthermore, the nucleotide sequence could be amplified prior to hybridization by the methods described above.

Once specific sequences are shown to be associated with *C. jejuni*, the methods to detect specific sequences are standard in the art. Detection of specific sequences using direct probing involves the use of oligonucleotide probes which may be prepared, for example, synthetically or by nick translation. The probes may be suitably labeled using, for example, a radio label, enzyme label, fluorescent label, biotin-avidin label and the like for subsequent visualization in the example of Southern blot hybridization procedure. The labeled probe is reacted with a bound sample DNA, e.g., to a nitrocellulose sheet under conditions such that only fully complementary sequences hybridize. The areas that carry DNA sequences complementary to the labeled DNA probe become labeled themselves as a consequence of the reannealing reaction. The areas of the filter that exhibit such labeling may then be visualized, for example, by autoradiography. The label probe is reacted with a DNA sample bound to, for example, nitrocellulose under conditions such that only fully complementary sequences will hybridize. The stringency of hybridization is usually 5° C. below the Ti (the irreversible melting temperature of the hybrid formed between the probe and its target sequence) for the given chain length. For 20 mers, the recommended hybridization temperature is about 58° C. The washing temperatures are unique to the sequence under investigation and need to be optimized for each variant.

Alternative probing techniques, such as a ligase chain reaction (LCR), involve the use of mismatch probes, i.e., probes which are fully complementary with the target except at the point of the mutation. The target sequence is then allowed to hybridize both with oligonucleotides which are fully complementary and have oligonucleotides containing a mismatch, under conditions which will distinguish between the two. By manipulating the reaction conditions, it is possible to obtain hybridization only where there is full complementarity. If a mismatch is present, there is significantly reduced hybridization.

The polymerase chain reaction (PCR) is a technique that amplifies specific DNA sequences with remarkable efficiency. Repeated cycles of denaturation, primer annealing and extension carried out with polymerase, e.g., a heat stable enzyme Taq polymerase, leads to exponential increases in the concentration of desired DNA sequences. Given a knowledge of the nucleotide sequence of a mutation, synthetic oligonucleotides can be prepared which are complementary to sequences which flank the DNA of interest. Each oligonucleotide is complementary to one of the two strands. The DNA can be denatured at high temperatures (e.g., 95° C.) and then reannealed in the presence of a large molar excess of oligonucleotides. The oligonucleotides, oriented with their 3' ends pointing towards each other, hybridize to opposite strands of the target sequence and prime enzymatic extension along the nucleic acid template in the presence of the four deoxyribonucleotide triphosphates. The end product is then denatured again for another cycle. After this three-step cycle has been repeated several times, amplification of a DNA segment by more than one million-fold can be achieved. The resulting DNA may then be directly sequenced in order to locate any genetic alteration.

Alternatively, it may be possible to prepare oligonucleotides that will only bind to altered DNA, so that PCR will only result in multiplication of the DNA if a mutation is present. Following PCR, direct visualization of allele-specific oligonucleotide hybridization may be used for typing C. jejuni strain associated with an outbreak. Alternatively, an adaptation of PCR called amplification of specific alleles (PASA) can be employed; this uses differential amplification for rapid and reliable distinction between alleles that differ at a single base pair. Other techniques, such as 3SR, which utilize RNA polymerase to achieve high copy number, can also be used where appropriate.

In yet another method, PCR may be followed by restriction endonuclease digestion with subsequent analysis of the resultant products. Nucleotide substitutions can result in the gain or loss of specific restriction endonuclease site. The gain or loss of a restriction endonuclease recognition site facilitates the typing of the C. jejuni strains associated outbreak using restriction fragment length polymorphism (RFLP) analysis or by detection of the presence or absence of a polymorphic restriction endonuclease site in a PCR product that spans the sequence of interest.

For RFLP analysis, DNA is obtained, for example from the stool of the subject suspected of containing C. jejuni, or C. jejuni isolated from subject, is digested with a restriction endonuclease, and subsequently separated on the basis of size by agarose gel electrophoresis. The Southern blot technique can then be used to detect, by hybridization with labeled probes, the products of endonuclease digestion. The patterns obtained from the Southern blot can then be compared. Using such an approach, PEB1A DNA is detected by determining the number of bands detected and comparing this number to the DNA from C. jejuni strains that are not associated with the C. jejuni outbreak. Restriction endonucleases can also be utilized effectively to detect mutations in the PEB1A gene.

Similar creation of additional restriction sites by nucleotide substitutions at the disclosed mutation sites can be readily calculated by reference to the genetic code and a list of nucleotide sequences recognized by restriction endonucleases.

In general, primers for PCR and LCR are usually about 20 bp in length and the preferable range is from 15–25 bp. Better amplification is obtained when both primers are the same length and with roughly the same nucleotide composition. Denaturation of strands usually takes place at 94° C. and extension from the primers is usually at 72° C. The annealing temperature varies according to the sequence under investigation. Examples of reaction times are: 20 mins denaturing; 35 cycles of 2 min, 1 min, 1 min for annealing, extension and denaturation; and finally a 5 min extension step.

PCR amplification of specific alleles (PASA) is a rapid method of detecting single-base mutations or polymorphisms. PASA (also known as allele specific amplification) involves amplification with two oligonucleotide primers such that one is allele-specific. The desired allele is efficiently amplified, while the other allele(s) is poorly amplified because it mismatches with a base at or near the 3' end of the allele-specific primer. Thus, PASA or the related method of PAMSA may be used to specifically amplify the mutation sequences of the invention. Where such amplification is done on C. jejuni isolates or samples obtained from an individual during outbreak, it can serve as a method of detecting the presence of the mutations in the strain responsible for the cause of the outbreak.

As mentioned above, a method known as ligase chain reaction (LCR) can be used to successfully detect a single-base substitution. LCR probes may be combined or multiplexed for simultaneously screening for multiple different mutations. Thus, LCR can be particularly useful where, as here, multiple mutations are predictive of the C. jejuni strain that is specifically associated with an outbreak.

Antigen-Detecting Kit The present invention provides a kit for the diagnosis of infection by strains of C. jejuni. Particularly, the kit can detect the presence of PEB1A antigen specifically reactive with an antibody or an immunoreactive fragment thereof. The kit can include an antibody bound to a substrate, a secondary antibody reactive with the antigen and a reagent for detecting a reaction of the secondary antibody with the antigen. Such a kit can be an ELISA kit and can comprise the substrate, primary and secondary antibodies when appropriate, and any other necessary reagents such as detectable moieties, enzyme substrates and color reagents as described above. The diagnostic kit can, alternatively, be an immunoblot kit generally comprising the components and reagents described herein.

Antibody-Detecting Kit

The diagnostic kit of the present invention can be used to detect the presence of a primary antibody specifically reactive with PEB1A or an antigenic fragment thereof. The kit can include the antigen bound to a substrate, a secondary antibody reactive with the antibody specifically reactive with the PEB1A antigen and a reagent for detecting a reaction of the secondary antibody with the primary antibody. Such a kit can be an ELISA kit and can comprise the substrate, antigen, primary and secondary antibodies when appropriate, and any other necessary reagents such as detectable moieties, enzyme substrates and color reagents as described above. The diagnostic kit can, alternatively, be an immunoblot kit generally comprising the components and reagents described herein.

Nucleic Acid Detection (Diagnostic) Kits

Once the nucleotide sequence of the PEB1A antigen is determined, the diagnostic kit of the present invention can alternatively be constructed to detect nucleotide sequences specific for the antigen comprising the standard kit components such as the substrate and reagents for the detection of nucleic acids. Because C. jejuni infection can be diagnosed by detecting nucleic acids specific for the antigen in intestinal tissue and stool, it will be apparent to an artisan that a kit can be constructed that utilizes the nucleic acid detection methods, such as specific nucleic acid probes, primers or restriction fragment length polymorphisms in analyses. It is contemplated that the diagnostic kits will further comprise a positive and negative control test.

The particular reagents and other components included in the diagnostic kits of the present invention can be selected from those available in the art in accord with the specific diagnostic method practiced in the kit. Such kits can be used to detect the antigen in tissue and fluid samples from a subject.

The following examples are intended to illustrate, but not limit, the invention. While they are typical of those that might be used, other procedures known to those skilled in the art may be alternatively employed.

EXAMPLE 1

Cloning and expression of PEB1A antigen bacterial strains and growth conditions.

C. jejuni strain 81-176 (ATCC 55026) was used to clone the gene for the PEB1A antigen. Twelve clinical Campylobacter isolates from humans, including 5 C. jejuni, 3 C. coli, 2 C. lari, and 2 C. fetus strains were used to assess conservation of the gene (Table 1). Stock cultures were maintained at −70° C. in Brucella broth (BBL Microbiology Systems, Cockeysville, Md.) supplemented with 15% glycerol. Campylobacter strains were cultured in Brucella broth supplemented with 5% sheep blood in a microaerobic atmosphere (generated by CampyPak-Plus (BBL) at 37° C. for 48 hours. For transformation and protein expression, E. coli strains XL1-Blue, Y1088, Y1089, Y1090 (Stratagene, La Jolla, Calif.) were cultured in Luria-Bertoli (LB) medium with shaking at 37° C. The final concentrations of carbonicillin when added to media was 50 μg/ml.

Chemicals and Enzymes

Isopropyl-β-D-thiogalactopyranoside (IPTG) was purchased from Sigma Chemical Co. (St. Louis, Mo.) and used at 57 μg/ml, and 5-bromo-4-chloro-3-indolyl-β-D-galactoside (X-GAL; final concentration 40 μg/ml) was from Boehringer-Mannheim (Indianapolis, Ind.). Restriction enzymes, T4 DNA ligase, E. coli DNA polymerase large (Klenow) fragment and SEQUENASE (bacteriophage $T_7$ DNA polymerase) were from Promega and United States Biochemicals (Cleveland, Ohio). [α-$^{32}$P] dATP (650 Ci/mmol) was from ICN Radiochemicals (Irvine, Calif.).

Genetic techniques and nucleotide sequence analysis.

To obtain chromosomal DNA from C. jejuni strain 81-176 the strain was cultured for 48 h in Brucella broth, the cells pelleted, and resuspended in 50 mM Tris-HCl (ph 8.0) containing 25% sucrose. Cells were lysed using lysozyme. After chloroform-phenol extractions, the chromosomal DNA was precipitated with 70% ethanol containing ammonium acetate at a final concentration of 0.75M. Plasmids were isolated by the rapid alkaline extraction procedure of Birnboim and Doly (*Nucleic Acids. Res.*, 7:1513–1523, 1979) and purification was completed by precipitation in the presence of 800 mM NaCl and 6.5% polyethylene glycol. All other standard molecular genetic techniques, including sequential ordered deletions, were performed as described (Sambrook et al. *Molecular cloning: A Laboratory Manual*, 1989). The nucleotide sequence was determined unambiguously on both strands using double-stranded DNA templates and the dideoxy chain termination procedure as described previously (Sanger et al. *Proc. Natl. Acad. Sci. U.S.A.*, 71:1342–1346.32, 1977). Oligonucleotide primers were synthesized by the Vanderbilt University DNA Core Facility using a Milligen 7500 DNA synthesizer, using the manufacturer's protocol. Nucleotide sequences were compiled and analyzed with the aid of the DNA-Star program (DNA Star, Inc., Madison, Wisc.).

Construction of a genomic library from C. jejuni.

Strain 81-176 chromosomal DNA was sheared by sonication and the resulting mixture containing random fragments of up to 10 kb were passed over a sepharose CL2B column and the fractions eluting in the void volume were pooled. The DNA was treated with T4 DNA polymerase to produce blunt ends, and ligated to phosphorylated EcoRI octamer linkers (New England Biolabs, Beverly, Mass.). The DNA was digested with EcoRI and ligated to the EcoRI arms of the λgt11 vector, according to the manufacturer's protocol. The ligation mixtures were added to a packaging mix (Stratagene) and titered on Y1088 cells.

Cloning of C. jejuni-specific genes

Polyclonal antiserum to the PEB1A protein purified from strain 81-176. was raised in hyperimmunized rabbit as previously described (Pei, et al. 1991. *J.Biol.Chem.* 266:16363–16369). Before use, cross-reacting anti-E. coli antibodies were removed by absorption with a lysate prepared from E. coli Y1089 λgt11 lysogen. The amplified phage library was then screened by allowing approximately 105 plaques to grow on Y1090 cells for 2.5 h at 42° C., overlaying with a nitrocellulose filter previously impregnated with 10 mM IPTG, and incubating for 2 h at 37° C. The filters were then screened with the adsorbed serum to detect reactive clones. Positive plaques were purified, and lysates were prepared from these infected E. coli cells. The lysates were immunoblotted with the adsorbed serum and clones expressing recombinant proteins were saved. Screening of approximately $10^5$ plaques yielded two strongly positive signals. All two were plaque-purified and each recombinant phage used to make lysates of Y1090 cells. By immunoblotting with the antiserum to PEB1A, each of the Y1090 lysates showed a strongly immunoreactive band migrating at either approximately 28 kDa (FIG. 1).

For expressing and mapping the insert, the original clones in λgt11 were used to prepare purified phage DNA. The phage DNA was digested with EcoRI, the insert was separated in low melting point agar and ligated into the EcoRI site of pUC19. The ligation mixture was used to transform competent XL-I Blue E. coli cells, and carbenicillin-resistant transformants isolated. The resulting clone is called pPB119. After plasmid purification, restriction enzyme cleavage maps were generated (FIG. 2) and the plasmid used for further characterization.

Southern hybridization.

Campylobacter chromosomal DNA was digested with HindIII and the resulting fragments were electrophoresed on a 0.7% agarose gel in 0.04M Tris-acetate-2 mM EDTA buffer (pH 8.2). All hybridization conditions and procedures were exactly as described (Sambrook et al, 1989). Probes were radiolabeled by primer extension using random hexamers (Feinberg and Bogelstein, *Anal. Biochem*, 132:6–13, 1983). Hybridization was carried out at 42° C. overnight in buffer containing 50% formamide and exposed to XAR-2 X-ray film (Eastman Kodak, Rochester, N.Y.).

Colony hybridization.

Campylobacter strains were grown on trypticase soy blood agar plates (BBL) and replica copies of these colonies were transferred to nitrocellulose filters. Each filter was placed on 3 mm Whatman paper saturated with 0.2M NaOH/1.5M NaCl. After 3 min the filter was transferred to 3 mm Whatman paper saturated with 0.4M Tris-Cl (pH 7.6)/2×SSC (1×SSC is 0.15M NaCl, 0.015M Sodium citrate) for 3 min, and then to 2×SSC for 3 min. The colony blot filters were dried in a vacuum oven for 90 min at 80° C. and hybridized with radiolabeled PEB1A gene as described (Sambrook et al, 1989).

Mapping the pUC19 insert.

Figure 2:
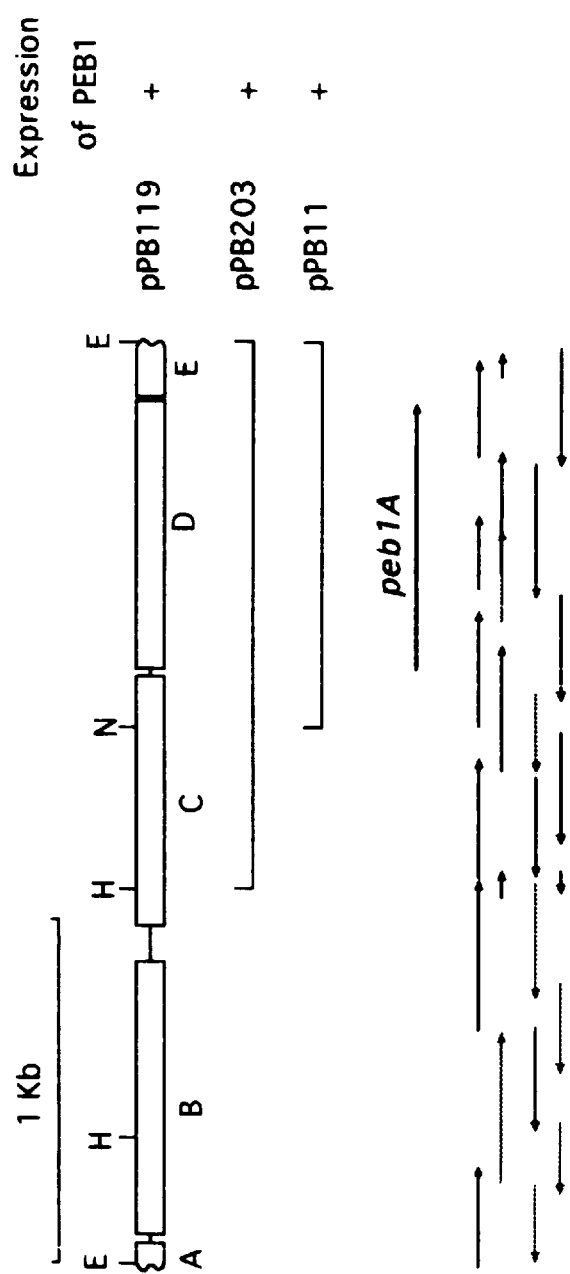

After digestion with EcoRI, plasmid pPB119 was found to contain DNA insert of approximately 2.6 kb. Analysis of deletion mutants pPB203 and PPB11 produced by restriction enzymes HindIII and NcoI, identified the orientation and approximate location of the open reading frame (ORF) for PEB1A (peb1A) (FIG. 2, large arrow).

Sequence analysis of peb1A.

To determine the sequence of the 2.6 kb insert in pPB119, a series of nested ordered deletions of the plasmid using exonuclease III and restriction enzymes was performed, as described (Sambrook et al., 1989). In total, the sequence for the entire pPB119 insert representing 2687 bp was determined on both strands (SEQ ID NO: 10). The nucleotides are numbered on the right of each line. SEQ ID NO: 8 provides the deduced amino acid sequence of the open reading frame D(ORF D) encoding PEB1A shown in SEQ ID NO: 7. The nucleotide sequence of the 2687 kb insert determined according to the strategy shown in FIG. 2 yielded three complete and two partial open reading frames (ORFS) which were designed 5' to 3' as ORFs A (SEQ ID NO:1), B (SEQ ID NO:3), C (SEQ ID NO:5), D (SEQ ID NO:7), and E (SEQ ID NO:9) (FIG. 2). ORF A (SEQ ID NO:1) is a partial ORF encoding 21 amino acids ending with TAA at positions 65–67. Between ORF A (SEQ ID NO:1) and ORF B (SEQ ID NO:3) there are 15 nucleotides in addition to the stop condon of ORF A (SEQ ID NO:1) containing a putative ribosomal binding site AGGA (positions 72–75) 7 (SEQ ID NO:3) nucleotides upstream from the ATG initiating ORF B (SEQ ID NO:3). No putative transcriptional terminator was found in this region, suggesting that ORFs A and B (SEQ ID NO:3) may be co-transcribed. ORF B is 792 nucleotides, encoding a 264 residue polypeptide, ending with TAA at position 811–813. Following ORF B (SEQ ID NO:3) is a 131-nucleotide noncoding sequence containing an inverted repeat that could form a stem-loop structure ($\Delta G=-9.0$). ORF C (SEQ ID NO:5) begins with an unusual start codon TTG at positions 132–134. A putative ribosomal-binding site (AGGA) is located 6 nucleotides upstream from the TTG. There is a sequence (TAAAAT) resembling the –10 consensus sequence in *E. coli* (TAtAaT), that is 35 bases upstream from the ribosome-binding site, and 20 nucleotides further upstream there is a sequence (TTGAAG) resembling the –35 consensus sequence in *E. coli* (TTGACa). ORF C (SEQ ID NO:5) is 729 nucleotides encoding a polypeptide of 242 amino acids, ending at positions 858–860 with TAA. ORF D (SEQ ID NO:7) follows ORF C (SEQ ID NO:5) after a 21 nucleotide noncoding region the stop condon that terminates ORF C (SEQ ID NO:5). A putative ribosomal binding site (AGGA) is located 6 nucleotides upstream from the start codon (ATG) for ORF D at position (SEQ ID NO:7) 25. ORF D (SEQ ID NO:7) (peb1A) is 780 nucleotides, terminated by TAA at positions 802–804, and encodes a polypeptide of 259 amino acids with molecular mass of 28.18 kDa. One base downstream of ORF D )SEQ ID NO:7) the truncated ORF E (SEQ ID NO:9) begins; only the first 50 amino acids of this ORF can be deduced from the insert. Since no potential transcriptional terminators were found between ORFs C (SEQ ID NO:5), D (SEQ ID NO:7), and E (SEQ ID NO:9), it is possible that these ORFs are co-transcribed using a common promoter located upstream from ORF C (SEQ ID NO:5). No ORF greater than 300 nucleotides was found in the complementary strand.

Signal sequence of PEB1A.

The N-terminal amino acid sequence of the mature native PEB1A, given for example in SEQ. ID NO: 11 and at Table 2 of the grandparent application hereto, columns 9 and 10 of U.S. Pat. No. 5,200,344 (the antigen is there called "PEB1") is identical with the deduced sequence from ORF D (SEQ ID NO:7) beginning at residue (AS shown in SEQ ID NO:8), indicating that mature PEB1A had a 26-residue cleaved signal sequence. That the DNA sequence of SEQ ID NO:7 at nucleotide 103–105 predicts Ala for the first position of the mature protein whereas amino terminal sequencing showed Gly (as Shown in SEQ ID NO:4) may be artifactual since the chromatographic behaviors of the two amino acids during sequencing are similar. Overall, the 26 residue signal peptide has a calculated molecular weight of 2742 and is similar in structure to a typical signal peptide. Residues Arg and Lys at positions 4 and 5 form its positively-charged head, the next 9 residues form a hydrophobic core, followed by Gly, an a-helix breaker, 10 residues upstream from the cleavage site. A typical structure for signal peptidase I (SPI) cleavage occurs between residues Ala-26 and Ala-27 followed by negatively charged Glu-28. Immediately following the cleavage site, 8 of 13 residues are polar. A second conserved signal peptidase processing structure ($Leu_{15}$-$Gly_{16}$-$Ala_{17}$-$Cys_{18}$) homologous to signal peptidase II (SPII) cleavage sites was located, in which Cys is essential, Leu highly conserved, and small amino acids between Leu and Cys such as Gly, Ala, Ser, or Val preferred.

Homologies of PEB1A with other proteins.

Search of the National Biomedical Research Foundation (PIR 21.0) showed 27.8% identity of the deduced peb1A product with *E. coli* glutamine-binding protein precursor (glnH) 22.9% with *Salmonella typhimurium* lysine-arginine-ornithine-binding protein (LAO), and 28.9% with *S. typhimurium* histamine-binding protein (hisJ). Searches of a variety of regions of PEB1A show no significant homologies with other known proteins. Amino acid composition, molecular weight, and secondary structure, are similar between PEB1A and glnH, hisJ and LAO; however, PEB1A is significantly more basic than these other proteins. A pair-wise alignment of the primary sequence did not show consecutive identical regions of more than four amino acid residues between PEB1A and glnH or LAO. The relationship of PEB1A with amino acid-binding proteins was further confirmed by the homology of ORF C (SEQ ID NO:5) with other members of operons for glutamine and histidine transport systems. ORF C (SEQ ID NO:5) shares nearly 50% identity with the proteins, glnQ and hisp, which serve as membrane receptors for the binding proteins glnH and hisJ, respectively. Both glnQ and hisP like ORF C (SEQ ID NO:5), begin with uncommon start codons such as TTG or GTG. The third member of the putative PEB1A operon, ORF E (SEQ ID NO:9) did not share significant homology with other known proteins in the limited sequence that was identified.

Conservation of peb1A gene among *C. jejuni* strains.

Figure 3:
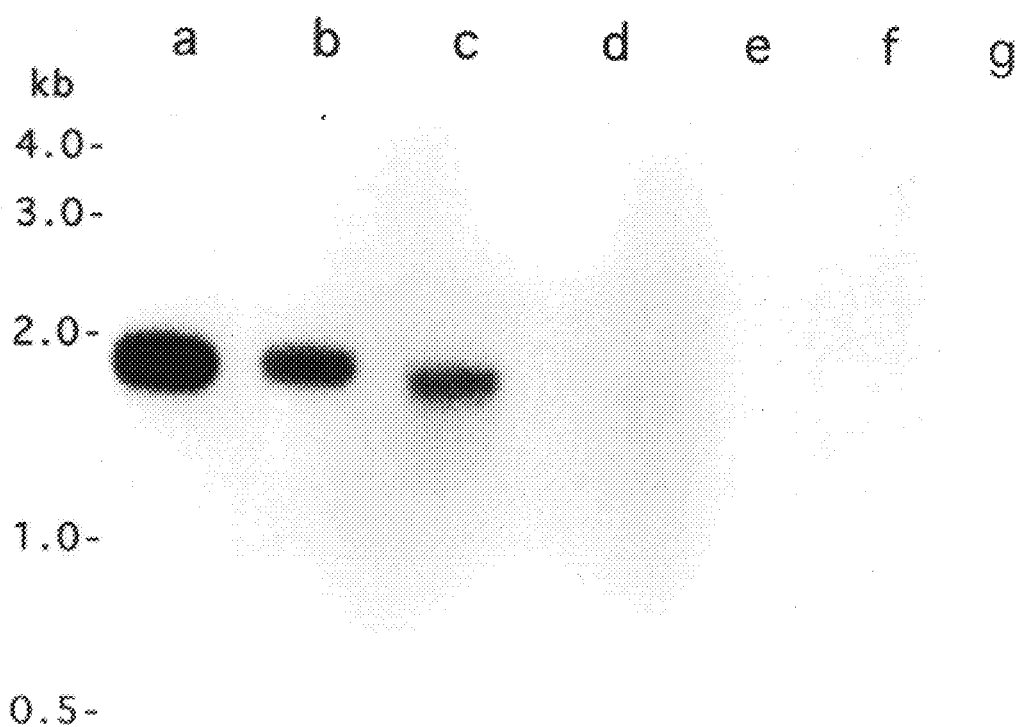
Figure 4B:
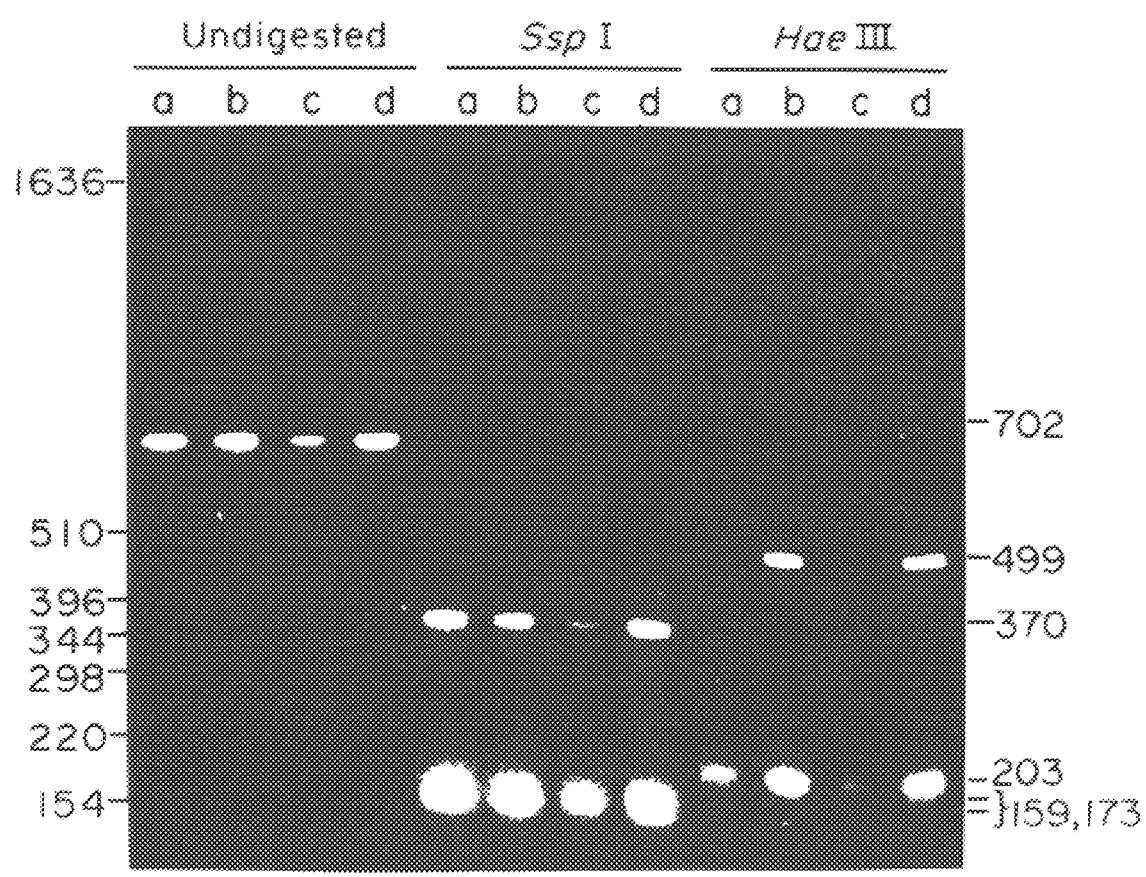

We next sought to determine the conservation of peb1A among Campylobacter strains by Southern hybridization since PEB1A is apparently present in all *C. jejuni* strains examined, and a closely-related molecule is found in *C. coli*. Initial analyses used as the probe a 702 bp PCR product from pPB119 (primers: 5'-GCAGAAGGTAAACTTGAG TCTATT- 3' (bp 103–126 of SEQ ID NO:7);

5'-TTATAAACCCCATTTTTTCGCTAA-3' (complimentary to bp 781–804 of SEQ ID NO:7)] corresponding to the start and end of the sequence encoding mature PEB1A). Under high stringency conditions, this probe hybridized to a single 1.8 kb HindIII-digested chromosomal fragment from all three C. jejuni strains but not to the other Campylobacter strains examined (FIG. 3). When the same pair of primers was used in PCR analysis, a 702 bp PCR product was amplified from all three C. jejuni strains tested as predicted, but from none of the C. coli, C. lari or C. fetus strains tested (FIG. 4A). Restriction digestion of the peb1A PCR products amplified from each of the three C. jejuni strains demonstrated identical patterns (FIG. 4B), exactly as expected from sequence analysis, indicating the high degree of conservation of the peb1A gene among C. jejuni strains.

The present example provides a cloned fragment of C. jejuni genomic DNA that includes a gene encoding an important C. jejuni antigen, PEB1A. The evidence that pPB119 contains the gene encoding the PEB1A is summarized as follows: 1) E. coli transformed into pPB119 expressed a protein similar in electrophoretic migration to PEB1A from C. jejuni. 2) The amino terminal sequence determined by peptide analysis of mature PEB1A matches that deduced from the peb1A DNA sequence. A leader peptide was predictable (and observed), since PEB1A does not have an amino-terminal methionine and is an exported protein. The deduced molecular mass of the mature peb1A product is 25.5 kDa, slightly less than that determined by SDS-PAGE (28 kDa), which could be due to the slower migration of a basic protein that has fewer net negative charges per residue.

The PEB1A gene is present in all eight C. jejuni strains tested, by PCR amplification or DNA hybridization. Using the same assays at high stringency conditions, PEB1A gene could not be amplified or hybridized with PEB1A gene from C. coli. These results indicate that although PEB1A gene is highly conserved in C. jejuni, the homolog in C. coli differs substantially. Thus, these assays can be used in rapid diagnosis of C. jejuni infection and in differentiation between C. jejuni and C. coli isolates.

As shown by the immunoblot study, a full length antigenic PEB1A product can be expressed in E. coli. Since pPB119 contains all essential genetic elements coding for PEB1A, expression of PEB1A to produce a recombinant PEB1A in native form in C. jejuni is possible. Use of this recombinant protein can readily supply sufficient antigen to aid in development of immunoassays to detect human serum antibodies to PEB1A for diagnostic purpose. Similarly, the recombinant protein can be used as vaccine to stimulate immune response to PEB1A for prevention and treatment of C. jejuni infection.

EXAMPLE 2

Construction and characterization of a PEB1A-negative strain of Campylobacter jejuni Bacterial strains, vectors and growth conditions.

C. jejuni strain 81-176 (ATCC 55026) used in this study was from the culture collection of the Vanderbilt University Campylobacter/Helicobacter Laboratory and was chosen because it has been extensively characterized. Stock cultures were maintained at −70° C. in Brucella broth (BBL Microbiology Systems, Cockeysville, Md.) supplemented with 15% glycerol. C. jejuni strains were grown on blood agar plates supplemented with vancomycin (10 mg/liter), polymyxin B (5000 U/liter), and trimethoprim (5 mg/liter) under microaerobic conditions at 37° C. for 48 hours. E. coli strain DH5α (Stratagene, La Jolla, Calif.) used for transformation, was grown in LB medium. As described above, pPB119 contains the PEB1A gene on a 2.6 kb insert in pUC19. Plasmid pILL600 (Labigne-Roussel et al. J.Bacteriol., 170:1704, 1988) was used as a source of a kanamycin (km) resistance gene.

Chemicals and enzymes.

Final concentrations of carbonicillin(50 µg/ml) and kanamycin (20 µg/ml) were used whenever necessary. Restriction enzymes, T4 DNA ligase, E. coli DNA polymerase large (Klenow) fragment were from Promega and United States Biochemicals (Cleveland, Ohio). α-$^{32}$P-dATP (650 Ci/mmol) was from ICN Radiochemicals (Irvine, Calif.).

Genetic techniques.

Chromosomal DNA was prepared as described above. Plasmids were isolated by equilibrium centrifugation in discontinuous Cs-ethidium bromide gradients (Sambrook, et al. 1989). All other standard molecular genetic techniques were performed as described (Sambrook, et al., 1989). DNA fragments used as probes for hybridization experiments were gel-purified.

Introduction of km cassette into C. jejuni strain 81-176.

Figure 5:
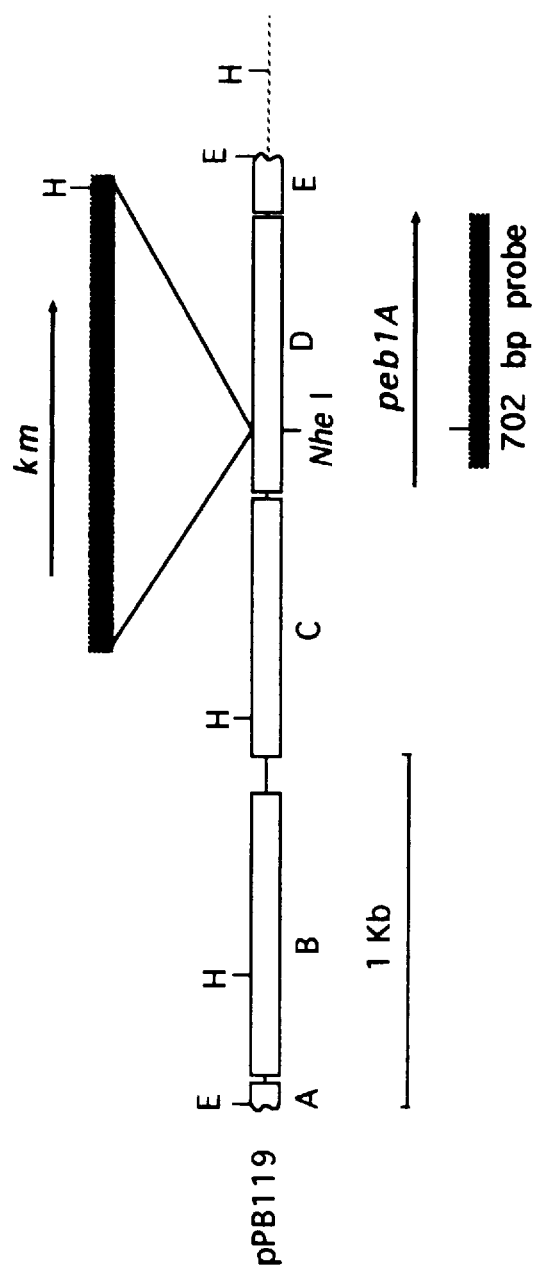

An E. coli kanamycin-resistance gene was inserted into the unique NheI C. jejuni site of pPB119 to create pPB119:km (FIG. 5). This construct was introduced directly into C. jejuni strain 81-176 by electroporation. Briefly, C. jejuni cells grown on blood agar plates for 48 h were harvested, washed three times in electroporation buffer (15% glycerol/5% sucrose) and suspended in ~50 µl of the buffer. Plasmid DNA from pPB119:km were added to the cells and transferred to 0.1 cm electroporation curvette in a Gene-pulsar apparatus (Bio-Rad), and high voltage pulses (25 F, 1.8 kv and 200 Ω) were delivered as described previously (Ferrero et al, J.Bacteriol., 174:4212, 1992). Following electroporation, the cells were suspended in 1 ml of LB media and spread on blood agar plages. The plates were incubated at 37° C. under microaerobic conditions for 24 h, then cells were harvested, plated on blood agar plates containing 20 µg/ml of kanamycin, and incubated microaerobically for 48 h.

The cloning vector used was unable to replicate in C. jejuni and selection on kanamycin-containing media yielded kanamycin-resistant recombinants. From approximately $10^{10}$ C. jejuni cfu, 300 transformants ($10^{-8}$) were obtained when 100 µg of plasmid DNA was used.

Colony hybridization.

25 kanamycin-resistant transformants obtained by electroporation were grown on blood agar plates and replica copies of these colonies were transferred to nitrocellulose filters. Each filter was placed on 3 mM Whatman paper saturated with 0.2M NaOH/1.5M NaCl. After 3 min the filter was transferred to 3 mM Whatman paper, saturated with 0.4M Tris-HCl (pH 7.6)/2×SSC for 3 min, and then to 2×SSC for 3 min. The colony blot filters were dried in a vacuum oven for 90 min at 80° C. and hybridized with radiolabeled pUC19 or the km-resistance gene, as described above. The colony blots were washed at 60° C. in 0.5×SSC and exposed to XAR-2 X-Ray film (Eastman Kodak, Rochester, N.Y.).

Gel electrophoresis and immunoblot analysis.

Figure 6:
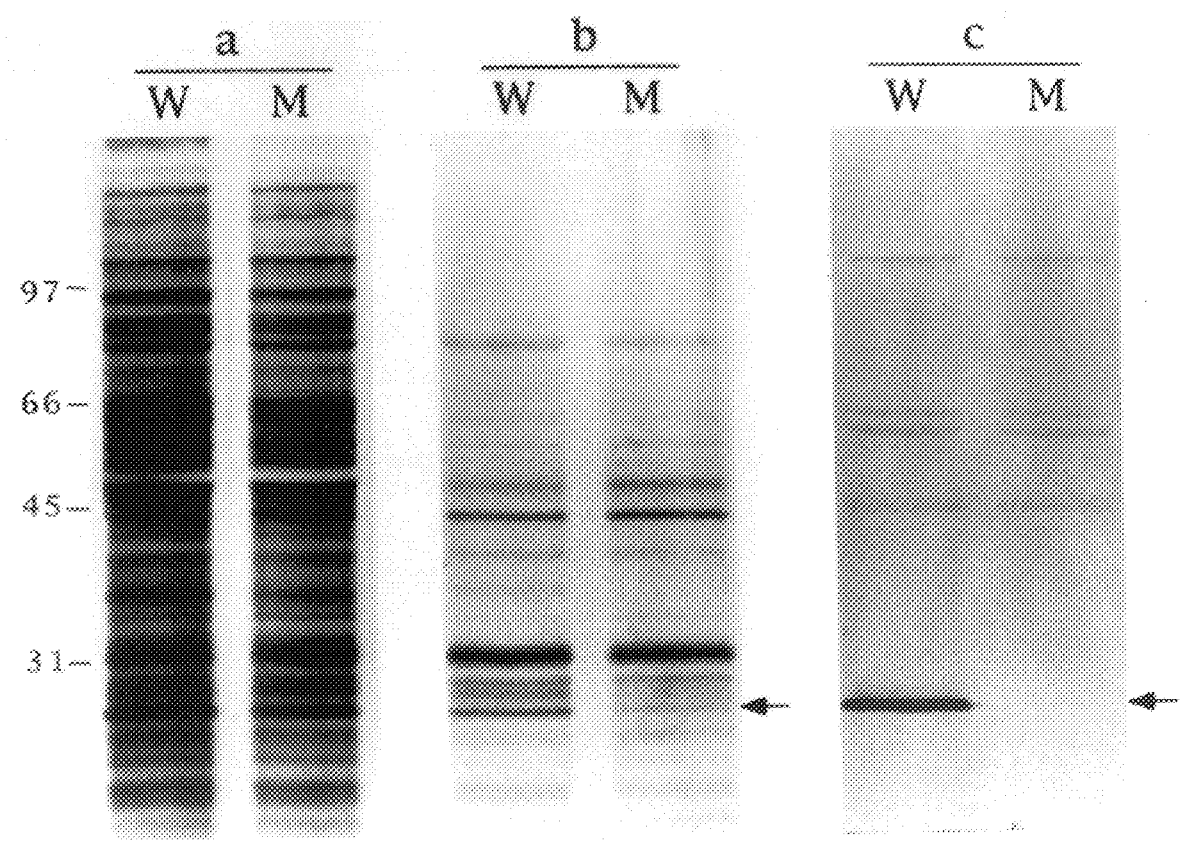

Immunoblotting of whole cell extracts derived from wild-type and mutants 4 was performed as detailed above using a 1:2000 dilution of antibody to PEB1A and a 1:2000 dilution of goat anti-rabbit IgG alkaline phosphatase conjugate as the secondary antibody, as described above. These studies showed that isogenic mutant strain 4 has no antigenic PEB1A gene product (FIG. 6).

Southern hybridizations.

C. jejuni chromosomal DNA was digested with HindIII or BamHI and PstI and the resulting fragments were electrophoresed on a 0.7% agarose gel and transferred to nylon membrane. Probes were Km-resistant gene and PEB1A gene, and were radiolabeled by primer extension using random hexameric oligonucleotides as described above. The DNA was then transferred to a nylon membrane and hybridized with $^{32}$P-labeled PEB1A gene or the 1.3 kb km cassette under conditions of high stringency with 50% formamide.
Genotypic characterization of the transformants.

To provide genetic evidence that the PEB1A gene is disrupted in the transformant strains, DNA isolated from wild-type strain 81-176 and C. jejuni mutant 4 was digested with the restriction endonuclease HindIII or BamHI and PstI. After separation of the digested DNA on an agarose gel the DNA was transferred to a nylon membrane and hybridized to PEB1A probe. This probe hybridized to approximately 8.6 kb BamHI-SacI fragment which is shifted to 10 kb in the mutant strain due to insertion of the Km cassette in PEB1A gene (data not shown). Similarly, a 1.8 kb HindIII fragment was lost and 2.2 kb and 0.7 kb fragments gained in mutant 4 because of the kanamycin resistance gene insertion. The kanamycin gene probe hybridized only with the 10 kb BamHI-PstI and 2.2 kb HindIII fragment in mutant 4, which indicate that replacement had occurred in the PEB1A gene. Thus, the PEB1A gene in strain 81-176 had been mutagenized by insertion of the km gene.

TABLE 1

Conservation of PEB1A gene in Campylobacter strains

| Strain designation | Presence of PEB1A band on immunoblot[a] | Hybridization with PEB1A gene probe[b] | Amplification of PEB1A gene[c] |
|---|---|---|---|
| C. jejuni | | | |
| 81-176 | ++ | + | + |
| 85-4 | ++ | + | ND |
| 81-95 | ++ | + | ND |
| b1916 | ++ | ND[d] | + |
| 85AC | ++ | ND | + |
| Positive/total | 5/5 | 3/3 | 3/3 |
| C. coli | | | |
| D126 | + | − | − |
| D730 | + | − | ND |
| D1035 | + | ND | − |
| Positive/total | 3/3 | 0/2 | 0/2 |
| C. lari | | | |
| D110 | − | ND | − |
| D67 | − | ND | − |
| Positive/total | 0/2 | 0/0 | 0/2 |
| C. fetus | | | |
| 23D | − | − | − |
| 84-91 | − | − | ND |
| Positive/total | 0/2 | 0/2 | 0/1 |

[a]. Recognition of PEB1A band in whole cell lysates by antibody to PEB1A as detected by immunoblot (Pei et al., 1991).
[b]. Hybridization of PEB1A gene to HindIII-digested chromosomal DNA in Southern blot (Sambrook et al., 1989).
[c]. Amplification of PEB1A gene from bacterial chromosomal DNA by PCR (Sambrook et al., 1989).
[d]. ND: not determined.

EXAMPLE 3

Role of PEB1A Leader Peptide in Exporting the Recombinant Protein

Figure 7:
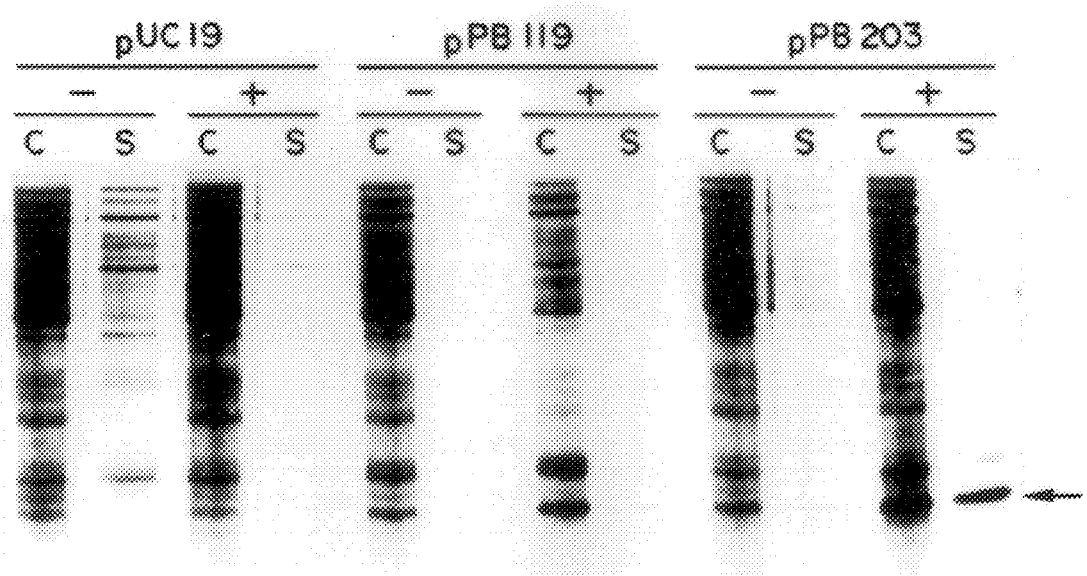

Expression of recombinant proteins in E. coli permits production of foreign proteins in large quantity. For the purpose of utilization of recombinant proteins, subsequent purification may be necessary. The difficulty to purify a recombinant protein depends on the subcellular location of the foreign protein. If a foreign protein expressed is located in cytoplasm or periplasmic space in E. coli, further purification of the protein will be difficult due to the contamination by E. coli proteins. E. coli does not routinely export its own proteins across the outer membrane, therefore the extracellular compartment (the culture media) is relatively clean and free of E. coli proteins. Thus, it would be ideal to express and export a recombinant protein in E. coli. Export of protein is often a function of its leader peptide which is the most amino-terminal part of the full length protein and is cleaved during maturation of the protein. A majority of leader peptides are only able to help the protein to cross the inner membrane of bacteria, resulting in a periplasmic space-located protein. The following experiments provide an example that the leader peptide of PEB1A of C. jejuni is able to export the recombinant protein from E. coli into culture supernatant.
Materials For transformation and expression of PEB1, E. coli XL1-Blue (Stratagens, La Jolla, Calif.) was cultured in LB medium with shacking at 37° C. The final concentration of carboniccilin at 50 μg/ml was added to the media, and 2 um IPTG (Sigma Chemical Co., St. Louis, Mo.) was added to the media to induce expression of the PEB1A. pPB119 was the source of PEB1A gene.
Exportation of PEB1A from E. coli A 1.0 kb segment upstream the PEB1A gene between EcoRI and HindIII sites (FIG. 2) is deleted from pPB119. The remaining plasmid was blunt-ended with klenow large fragment (Promega) and religated to generate pPB203. These procedures brought PEB1A gene closer to the IPTG-inducible lacZ promoter in the vector. After transformation, E. coli strain XL1-Blue harboring pPB203 was cultured in LB medium overnight at 37° C. in the presence of 50 μg/ml of carbonicillin and 2 μM IPTG. The culture was then adjusted to O.D.$_{600}$=1.0 with LB medium. Cells were pelleted and resuspended with LB medium to the precentrifugation volume, called cells. The culture supernatants were saved. The cells and culture supernatants were tested for presence of PEB1A by SDS-PAGE (FIG. 7). FIG. 7 shows that (1) in the absence of IPTG induction, deletion of the 1.0 kb EcoRI-HindIII fragment has no effect on expression of PEB1A, (2) with IPTG induction, cell associated PEB1 increased several fold in pPB203 compared with pPB119, and that PEB1 is exported into the culture supernatant at a level of approximately 4 μg/ml with about 70% purity.
Splicing and subcloning PEB1 leader sequence from pPB203

Once the DNA sequence for the leader peptide is provided, splicing of this sequence can be accomplished by several available methods directly or indirectly. PEB1A leader peptide contains 26 amino acids encoded by 78 base oligonucleotides (SEQ. ID. No. 7). The DNA of this size can be easily synthesized using standard DNA synthesis techniques such as Milligen 7500 automated DNA synthesizer. To facilitate subcloning of this leader sequence, extra DNA sequences of 6–10 base pairs encoding endonucleotide restriction enzyme cutting sites of interest can be designed to attach to the ends of the leader sequence during synthesis. Both strands should be synthesized and annealed at 37° C. to form a double-stranded DNA molecule. Both ends are then cut with restriction enzymes appropriate to the cutting sites chosen. The leader sequence can then be subcloned into a vector having corresponding sites in the polylinker region. Suitable vectors include most commonly used plasmid vectors such as pUC, M13 and pBluescript.

To express and export a protein of interest, the DNA fragment encoding the protein may be inserted in-frame at 3' end of the leader sequence. Under the induction of a promoter located upstream of the leader sequence, a fusion protein containing the leader peptide and the protein of interest will be expressed. In hosts such as E. Coli, the leader peptide will be cleaved from the protein of interest during exportation of the protein. Thus, such a strategy to produce a recombinant protein has two unique advantages: (1) the recombinant protein is exported into the culture supernatant so that subsequent purification is simple and easy; (2) the leader peptide is cleaved from the protein of interest during protein transportation so that artificial cleavage of the leader in vitro is not necessary. Other methods also can be used to splice the DNA sequence for the leader peptide. PCR is widely used to amplify a special DNA sequence of interest from a DNA template. To amplify the leader sequence, plasmid pPB119 or pPB203 can be used as template, two oligonucleotides of about 15–25 bases can be synthesized corresponding to the 5' ends of the coding and complimentary strands of the 78 base leader sequence. As mentioned above, to facilitate subcloning of the leader sequence, extra DNA sequence of 6–10 base pairs encoding restriction enzyme cutting sites of interest can be designed to attach to the 5' ends of each oligonucleotide during synthesis. These two oligonucleotides will be used as primers to amplify the leader sequence from pPB119 by polymerase chain reaction ("PCR") for 30 cycles. The amplified product may then be cut by the corresponding restriction enzymes at both ends, and subcloned into vectors of interest as described above.

Various publications are referenced throughout this application. The disclosures of these publications in their entireties are hereby incorporated by reference into this application in order to more fully describe the state of the art to which this invention pertains.

Although the present invention has been described in relation to particular embodiments thereof, many other variations and modifications and other uses will become apparent to those skilled in the art. By way of example, and without limitation, nonessential amino acids of a polypeptide of nucleotides of a DNA sequence may be deleted, replaced or added to so long as the function of the peptide (or encoded peptide) is not adversely effected. Naturally, codons may be freely interchanged with other codons specifying the same amino acid, even for a critical amino acid. The present invention is limited not by the specific disclosure herein, but is defined by the claims.

What is claimed is:

1. An isolated DNA fragment comprising a DNA sequence encoding a PEB1A antigen having SEO ID No. 8.

2. An isolated DNA fragment comprising nucleotides 25 through 804 shown in SEQ ID No. 7.

3. A recombinant expression vector comprising a DNA sequence encoding a PEB1A antigen having SEO ID No. 8.

4. A host cell transformed or transfected with the expression vector of claim 3.

5. A recombinant expression vector comprising a DNA sequence which includes nucleotides 25 through 804 shown in SEQ ID NO: 7.

6. A host transformed or transfected with the expression vector of claim 5.

7. The isolated DNA fragment, as recited in claim 1, further comprising a leader sequence.

8. The isolated DNA fragment, as recited in claim 7, wherein said leader sequence comprises nucleotides 25 through 102 of SEQ ID No. 7.

9. The recombinant expression vector, as recited in claim 3, further comprising a leader sequence.

10. The recombinant expression vector, as recited in claim 9, wherein said leader sequence comprises nucleotides 25 through 102 of SEQ ID No. 7.

11. The host cell, as recited in claim 4, wherein said vector further comprises a leader sequence.

12. The host cell, as recited in claim 1, wherein said leader sequence comprises nucleotides 25 through 102 of SEQ ID No. 7.

13. An isolated DNA fragment comprising nucleotides 25 through 102 of SEQ ID No. 7.

14. A recombinant expression vector comprising a DNA sequence which includes nucleotides 25 through 102 of SEQ ID No. 7.

15. A host cell transformed or transfected with a recombinant expression vector comprising a DNA sequence which includes nucleotides 25 through 102 of SEQ ID No. 7.

16. An isolated DNA fragment comprising nucleotides 103 through 804 of SEQ ID No. 7.

17. A recombinant expression vector comprising a DNA sequence which includes nucleotides 103 through 804 of SEQ ID No. 7.

18. A host cell transformed or transfected with a recombinant expression vector which includes nucleotides 103 through 804 of SEQ ID No. 7.

* * * * *